(12) United States Patent
Gordon et al.

(10) Patent No.: US 6,607,911 B2
(45) Date of Patent: Aug. 19, 2003

(54) COMPOSITIONS AND METHODS RELATING TO CONTROL DNA CONSTRUCT

(75) Inventors: Joan Gordon, Old Orchard Beach, ME (US); Clark A. Rundell, Standish, ME (US)

(73) Assignees: Maine Molecular Quality Controls, Inc., Westbrook, ME (US); Maine Medical Center Research Institute, Scarborough, ME (US)

( * ) Notice: Subject to any disclaimer, the term of this patent is extended or adjusted under 35 U.S.C. 154(b) by 0 days.

(21) Appl. No.: 09/866,293

(22) Filed: May 25, 2001

(65) Prior Publication Data

US 2003/0065163 A1 Apr. 3, 2003

(51) Int. Cl.[7] .................. C12N 15/00; C12N 15/09; C12N 15/63; C12N 15/70; C12N 15/74; C12N 15/64; C12Q 1/68; C12P 19/34; C07H 21/04
(52) U.S. Cl. .................. 435/320.1; 435/6; 435/91.1; 435/91.4; 435/91.5; 536/23.1
(58) Field of Search .................. 536/23.1; 435/6, 435/91.1, 91.4, 91.5, 320.1

(56) References Cited

U.S. PATENT DOCUMENTS 5,677,124 A * 10/1997 DuBois et al. ........... 435/235.1

FOREIGN PATENT DOCUMENTS

WO        WO 00/46401        *  8/2000

OTHER PUBLICATIONS

Bouaboula, M. et al., "Standarization of mRNA Titration Using a Polymerase Chain Reaction Method Involving Co–amplification with a Multispecific Internal Control", J. Biol. Chem., vol. 267, pp. 21830–21838 (1992).*
Eggerding et al., 1995 Human Mutation 5:153–165.
Friedman et al., 1999, Clin. Chem. 45–929–931.
Gál et al., 1999, Mol. Gen. Genet. 260:569–573.
Kerem et al., 1990, Proc. Natl. Acad. Sci. U.S.A. 87:8447–8451.
Riodan et al., 1989, Sci 245:1066–1073.
Roberts et al., 2001, Nucleic Acids Res. 29:268–269.
Rosenstein et al., 1998, J. Pediatrics 132: 589–595.
Schwartz et al., 1999, Clin. Chem 45:739–745.
Zielenski et al., 1991, Genomics 10:214–228.

* cited by examiner

Primary Examiner—Kenneth R. Horlick
Assistant Examiner—Teresa Strzelecka
(74) Attorney, Agent, or Firm—Morgan, Lewis & Bockius, LLP

(57) ABSTRACT

The invention relates to novel control DNA constructs, and methods and kits for using and making the same, which provide comprehensive controls useful for quality assurance in the diagnostic detection of complex genetic diseases such as, but not limited to, cystic fibrosis, and for quality assurance in nucleic acid assays to detect components associated with an environmental condition or a biological organism.

13 Claims, 8 Drawing Sheets

FIG. 6A

AAAGAAAATATCATCTTTGGTGTTTCCTATGATGAATAT  AMPLIFIED SEGMENT OF WT
                                         CFTR EXON 10 CODING REGION

AAAGAAAATATCATCGGTGTTTCCTATGATGAATAT    AMPLIFIED SEGMENT OF DELTA F508
                                         CFTR EXON 10 CODING REGION

TTTCTTTTATAGTAGAAA    WT PROBE

CCACAAAGGATACTACTTATA    COMMON PROBE
         |
    FLUORESCENT
       LABEL

FIGURE 7A

```
AACAGCGCGC GACACAGAGT GAGCACTTGG CAACTGTTAG
CTGTTACTAA CCTTTCCCAT TCTTCCTCCA AACCTATTCC
AACTATCTGA ATCATGTGCC CCTTCTCTGT GAACCTCTAT
CATAATACTT GTCACACTGT ATTGTAATTG TCTCTTTTAC
TTTCCCTTGT ATCTTTTGTG CATAGCAGAG TACCTGAAAC
AGGAAGTATT TTAAATATTT TGAATCAAAT GAGTTAATAG
AATCTTTACA AATAAGAATA TACACTTCTG CTTAGGATGA
TAATTGGAGG CAAGTGAATC CTGAGCGTGA TTTGATAATG
ACCTAATAAT GATGGGTTTT ATTTCCAGAC TTCACTTCTA
ATGGTGATTA TGGGAGAACT GGAGCCTTCA GAGGGTAAAA
TTAAGCACAG TGGAAGAATT TCATTCTGTT CTCAGTTTTC
CTGGATTATG CCTGGCACCA TTAAAGAAAA TATCATCTTT
GGTGTTTCCT ATGATGAATA TAGATACAGA AGCGTCATCA
AAGCATGCCA ACTAGAAGAG GTAAGAAACT ATGTGAAAAC
TTTTTGATTA TGCATATGAA CCCTTCACAC TACCCAAATT
ATATATTTGG CTCCATATTC AATCGGTTAG TCTACATATA
TTTATGTTTC CTCTATGGGT AAGCTACTGT GAATGGATCA
ATTAATAAAA CACATGACCT ATGCTTTAAG AAGCTTGCAA
ACACATGAAA TAAATGCAAT TTATTTTTTA AATAATGGGT
TCATTTGATC ACAATAAATG CATTTTTCGA AATGG
```

FIGURE 7B

```
GCATTCGAAA TAATGGAGAT GCAATGTTCA AAATTTCAAC
TGTGGTTAAA GCAATAGTGT GATATATGAT TACATTAGAA
GGAAGATGTG CCTTTCAAAT TCAGATTGAG CATACTAAAA
GTGACTCTCT AATTTTCTAT TTTTGGTAAT AGGACATCTC
CAAGTTTGCA GAGAAAGACA ATATAGTTCT TGGAGAAGGT
GGAATCACAC TGAGTGGAGG TCAACGAGCA AGAATTTCTT
TAGCAAGGTG AATAACTAAT TATTGGTCTA GCAAGCATTT
GCTGTAAATG TCATTCATGT AAAAAAATTA CAGACATTTC
TCTATTGCTT TATATTCTGT TTCTGGAATT GAAAAAATCC
TGGGGTTTTA TGGCTAGTGG GTTAAGAATC ACATTTAAGA
ACTATAAATA ATGGTATAGT ATCCAGATTT GGTAGAGATT
ATGGTTACTC AGAATCTGTG CCCGTATCTT GGTGTCAGTG
TACCGGTTTG
```

COMPOSITIONS AND METHODS RELATING TO CONTROL DNA CONSTRUCT

STATEMENT REGARDING FEDERALLY SPONSORED RESEARCH OR DEVELOPMENT

The invention was made in part using funds obtained from the U.S. Government (National Institutes of Standards and Technology Contract No. 50-DKNB-0-90079) and the U.S. government may have certain rights in the invention.

BACKGROUND OF THE INVENTION

Nucleic acids encompass both deoxyribonucleic acid (DNA) and ribonucleic acid (RNA). DNA, present in all nucleated cells, carries the information needed to direct the synthesis of every protein in the body. A single alteration in the correct sequence of the four DNA bases (adenine, thymidine, guanine, and cytosine) may result in a defective protein. Depending upon the protein and the affected organism, the defect may range from inconsequential to life-threatening, or may be of intermediate severity. Diseases as diverse as cystic fibrosis, some types of cancer, sickle cell anemia, and atherosclerosis are known to result from specific genetic alterations.

RNA, the intermediary between DNA and protein, is the product of transcription of a DNA template. RNA assays are being performed with increasing frequency in research and clinical laboratories. This is due at least in part to the prevalence of RNA viruses such as the human immunodeficiency virus (HIV) that causes AIDS and the hepatitis C virus (HCV), and the development of drugs used in treating infections with RNA viruses. Precise testing for the presence of specific nucleic acid sequences for identification or monitoring of disease is important, and constructs comprising nucleic acids with known sequences are necessary for validation, calibration, and standardization of those tests.

Nucleic acid assays are routinely performed, either manually or by automated instrumentation, in numerous reference and clinical laboratories. A nucleic acid assay may be performed to detect the presence of foreign DNA or RNA, which may indicate infection with a foreign organism. For example, a variety of molecular assays are used to establish the presence and identity of nucleic acids from the human immunodeficiency virus-1 (HIV-1), Chlamydia, and other organisms causing sexually transmitted diseases. An individual's DNA may also be analyzed to detect, treat, and in some cases prevent genetic disease. Genotype determination of genes for Factor-V Leiden, hereditary hemochromatosis, lipoprotein lipase mutations, and cystic fibrosis have important implications for health management. The Human Genome Project holds the promise of many more examples of medically efficacious genetic diagnostic determinations. The recent discovery of the breast cancer associated gene (BRCA-1) has highlighted both the importance of screening individuals for predisposition to a disease, and also the attendant need for accurate, precise, reproducible, and controlled nucleic acid assays.

Nucleic acid testing of a patient derived specimen is a multi-step process. Failure of any step in the process leads to inaccurate clinical information with potentially serious outcome for the patient. The clinical nucleic acid testing protocol includes amplification of one or more DNA segments, and detection of product by any of a number of techniques including binding and detection of labeled probe, and/or restriction enzyme digestion and/or electrophoresis. The test may fail to give the correct result due to interfering substances, unsuitable reaction conditions, reagent problems or detection system failure. The test may be functioning in most aspects but have lost its sensitivity to detect specific mutations or to detect low levels of a given nucleic acid sequence. Some tests experience interference from unexpected polymorphisms or rare mutations and subsequently yield erroneous results. All of these errors may be detected by testing suitable known reference materials in parallel with the patient specimen. Detection of the expected signal from appropriate quality controls validates the testing process.

Current mutation detection technologies fall into two broad categories. The first group includes mutation-scanning technologies; such as single-strand conformational polymorphism (SSCP), modified double gradient gel electrophoresis (DG-DGGE), heteroduplex analysis (HET), various cleavage assays, and direct sequencing. These procedures are generally too difficult and time-consuming for most diagnostic laboratories. In the second group are methodologies more amenable to high throughput diagnostic testing. These include multiplex allele-specific diagnostic assay (MASDA), amplification refractory mutation system (ARMS), PCR followed by an oligonucleotide ligation assay and sequence-coded separation (PCR/OLA/SCS), PCR-mediated site-directed mutagenesis (PSM), and various versions of forward and reverse allele-specific oligonucleotide (ASO) dot blots. All of these assays begin with amplification of 200 to 500 base pair fragments from genomic DNA. Appropriate reference material for these assays should contain one or more of these genomic nucleic acid fragments.

In the field of molecular pathology and genetic testing, a quality control sample includes a reference DNA or reference RNA of known quantity and quality to evaluate the reliability of all steps of a test. Such reference nucleic acid is ideally as similar as possible to the test sample, is available containing combinations of all relevant mutations and polymorphisms, and also has broad applicability to all test formats. Additionally, the reference nucleic acid should be easily produced, quantitated, and packaged with minimal technical capability. Materials meeting these requirements, however, are not available. Reference materials in use include cultured cell lines and patient-based controls materials such as previously tested DNA. They also include DNA extracted and purified from cell lines or patient based specimens. These materials suffer, however, in that they are expensive, difficult to maintain, and limited with respect to the number of genetic diseases, organisms, and combinations of mutations and polymorphisms that they represent.

The need to rely on patient-derived control material also makes it difficult to provide sufficient reference products to cover the large variety of genetic disorders. This is especially problematic when testing for diseases caused by multiple mutations. For example, cystic fibrosis (CF) is a common hereditary disease affecting 1 in 3200 Caucasian newborns in the United States, but the wide variety of mutant alleles makes it difficult to assemble a comprehensive CF proficiency panel. At the NIST Nucleic Acid Workshop, Wayne Grody, Division of Medical Genetics at UCLA, acknowledged the lack of DNA standards and noted that the CAP/ACMG Biochemical and Molecular Genetics Resource Committee would like to dramatically increase the challenges offered.

Further, the unavailability of widely applicable controls is due in part to the variety of different technologies and techniques currently employed for a given diagnostic determination. For example, genetic determinations currently include the use of the polymerase chain reaction (PCR), the ligase chain reaction (LCR), branched DNA, allele specific hybridization, and direct sequence determination. In addition, so-called "home brew" produced primer oligonucleotides, and isotopically labeled or non-radioisotopic based probes are used in a variety of configurations in genetic testing, but without any systematic quality control materials, and hence without any validation.

The aforementioned factors, coupled with the lability of nucleic acids, make it virtually impossible to obtain standard reagents to qualitatively and/or quantitatively assess the overall accuracy, reliability, and efficiency of a laboratory assay.

Cystic fibrosis (CF) is an important genetic disease related to mutation in the cystic fibrosis transmembrane conductance regulator (CFTR) gene. Many of the most common disease causing mutations are in exon 10 and exon 11 of the CFTR gene, and thus, genetic screening for these mutations is advantageous for early diagnosis of CF. Genetic testing for CF, as well as many other diseases, typically begins with amplification of the nucleic acid segment of interest (e.g., exon 10 and 11), and therefore, controls for these tests must include the nucleic acid region to be amplified. Quality controls for genetic tests are required by federal law and good laboratory practice, but are currently unavailable commercially for CF testing. The invention described herein fulfills the urgent need for validation materials in a variety of molecular assays, including genetic testing for cystic fibrosis.

BRIEF SUMMARY OF THE INVENTION

The invention includes an isolated control DNA construct comprising a vector portion for expression in a cell and a target nucleic acid comprising two or more nucleic acid fragments wherein each fragment specifies a component associated with at least one of a disease state, an environmental condition, or a biological organism, wherein the component is different from a component specified by any other fragment present elsewhere in the construct, and wherein the 5'-most fragment is linked to the vector portion via a restriction site not present elsewhere in the construct, and wherein the 3'-most fragment is linked to the vector portion via a restriction site not present elsewhere in the construct, and further wherein each the fragment is flanked by a restriction site not present elsewhere in the construct.

In one aspect, each of the fragments are selected from the group consisting of fragments of the same gene, and fragments of different genes.

In another aspect, each of the fragments comprise at least one exon of a gene.

In yet another aspect, the exon further comprises an intronic border fragment.

In a further aspect, each of the fragments are selected from the group consisting of fragments from the same organism and fragments from different organisms.

In yet a further aspect, the exon is a cystic fibrosis transmembrane conductance regulator (CFTR) exon.

In another aspect, the CFTR exon is selected from the group consisting of exon 1, exon 2, exon 3, exon 4, exon 5, exon 6a, exon 6b, exon 7, exon 8, exon 9, exon 10, exon 11, exon 12, exon 13, exon 14a, exon 14b, exon 15, exon 16, exon 17a, exon 17b, exon 18, exon 19, exon 20, exon 21, exon 22, exon 23, and exon 24.

In another aspect, the CFTR exon is selected from the group consisting of exon 10 and exon 11.

In yet another aspect, the restriction site is selected from the group consisting of a BssH II site, a Csp45 I site, a Age I site, and a Nco I site.

In a further aspect, the restriction site linking the 5'-most fragment to the vector portion is BssH II.

In yet a further aspect, the 5'-most fragment is CFTR exon 10.

In another aspect, the restriction site linking the 3'-most fragment to the vector portion is Age I.

In a further aspect, the 3'-most fragment is CFTR exon 11.

In another aspect, the restriction site linking the 3' and 5' ends of each of the fragments within the construct is Csp45 I.

In yet another aspect, the exon 10 comprises a mutation or polymorphism associated with cystic fibrosis.

In a further aspect, the mutation is selected from the group consisting of a G480C mutation, a DI507 mutation, and a DF508 mutation.

In another aspect, the polymorphism is selected from the group consisting of a F508C polymorphism, a I507V polymorphism, and a I506V polymorphism.

In yet another aspect, the exon 11 comprises a mutation or polymorphism associated with cystic fibrosis.

In further aspect, the mutation is selected from the group consisting of a G542X mutation, a G551D mutation, an R553X mutation, an A559T mutation, and an R560T mutation.

In yet a further aspect, the polymorphism is selected from the group consisting of a F508C polymorphism, a I507V polymorphism, and a I506V polymorphism.

In another aspect, the fragments comprise a nucleic acid selected from the group consisting of a *Giardia lamblia* nucleic acid, a *Cryptosporidium parvum* nucleic acid, a human immunodeficiency virus nucleic acid, a hepatitis C virus nucleic acid, a factor V nucleic acid, a *Chlamydia trachomatis* nucleic acid, a *Mycobacterium tuberculosis* nucleic acid, a nucleic acid associated with hereditary hemochromatosis, a parvovirus B19 nucleic acid, a lipoprotein lipase gene, a methyltetrahydrofolate reductase gene, a beta cystathionase synthetase nucleic acid, a Factor II nucleic acid, a Factor VII nucleic acid, a Factor VIII nucleic acid, Factor IX nucleic acid, a prothrombin nucleic acid, and a nucleic acid comprising a translocation associated with hematologic disease.

In yet another aspect, the nucleic acid comprising a translocation associated with hematologic disease is a BCR/abl nucleic acid.

The invention includes a method of producing an isolated control DNA construct. The method comprises linking the 5'-most end of a nucleic acid fragment with a 3'end of a vector, or portion thereof, using a restriction site not present elsewhere in the construct and linking the 3'-most end of a nucleic acid fragment with the 5' end of the vector, or portion thereof, using a restriction site not present elsewhere in the construct, and further linking the 3' end of the 5'-most nucleic acid fragment with the 5' end of the 3'-most fragment using a restriction site not present elsewhere in the construct, wherein each fragment specifies a component associated with at least one of a disease state, an environmental condition, or a biological organism wherein the component is different from a feature in any other component present elsewhere in the construct.

The invention includes a kit for producing a control DNA construct. The kit comprises a vector and at least two nucleic acid fragments, wherein the vector comprises at least two restriction sites that do not appear elsewhere in the construct, and wherein each the fragment comprises a restriction site at each end wherein the restriction site does not appear elsewhere in the construct but is complimentary with a restriction site at the end of another fragment or with an end of the vector, and wherein each fragment specifies a component of at least one of a disease state, an environmental condition, or a biological organism, wherein the feature is different from a component specified by any other fragment present elsewhere in the construct, the kit further comprising an applicator, and an instructional material for the use thereof.

In one aspect, the kit further comprises a restriction endonuclease specific for the restriction site.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIGS. 6A, 6B and 6C show a diagram depicting the steps of the oligonucleotide ligation assay system.

FIG. 7A sets forth the nucleic acid sequence of CFTR exon 10 fragment as used herein (SEQ ID NO:9).

FIG. 7B sets forth the nucleic acid sequence of CFTR exon 11 fragment as used herein (SEQ ID NO: 10).

DETAILED DESCRIPTION OF THE INVENTION

Figure 1:
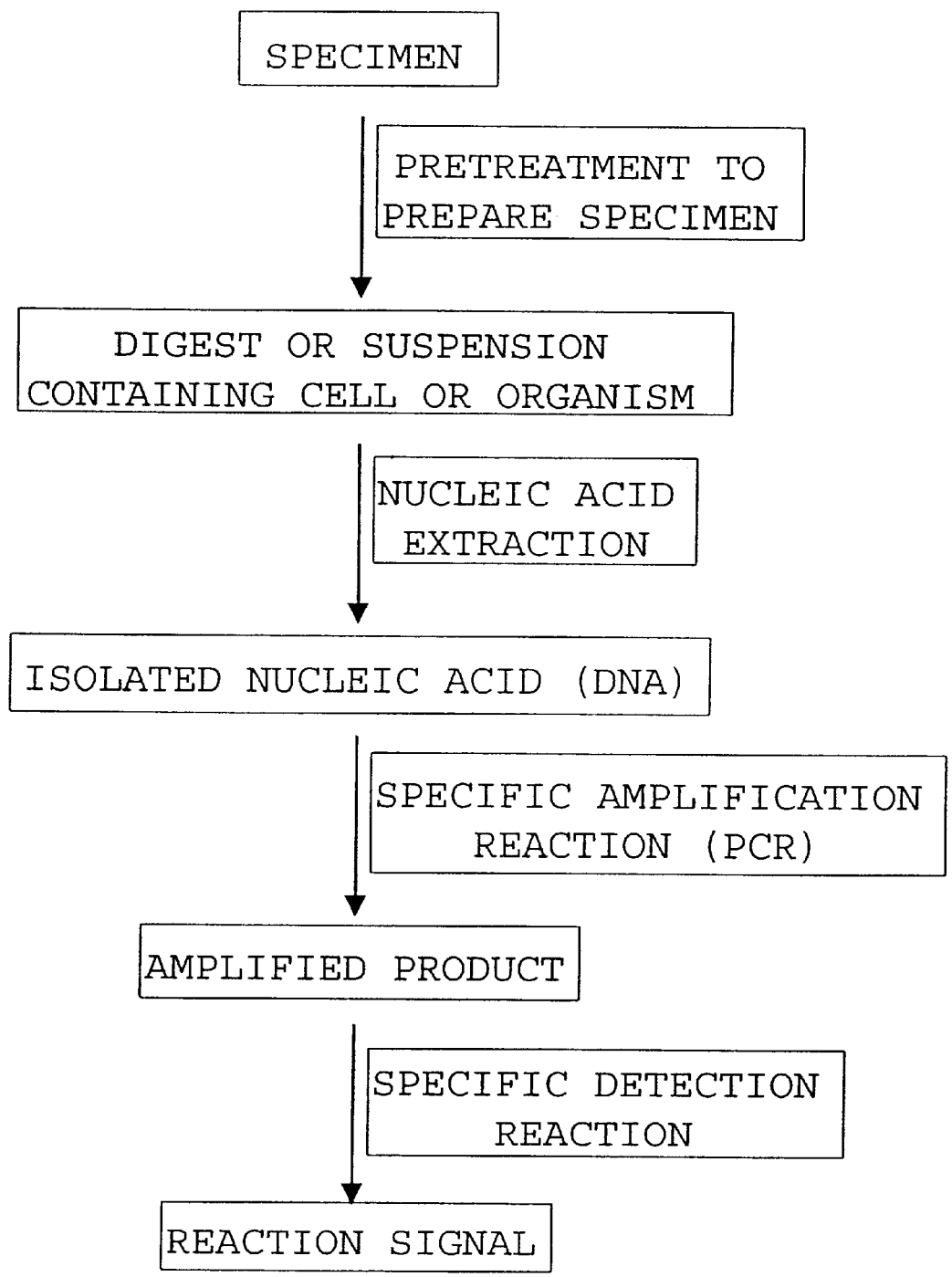
FIG. 1 is a diagram depicting the steps in nucleic acid testing.

The present invention relates to molecular standards for detection, diagnosis and characterization of nucleic acids, and mutants and variants thereof. The invention further relates to methods of producing such standards and uses therefor.

Definitions

As used herein, each of the following terms has following meaning.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering a nucleic acid, a binding agent, and the like, in a sample.

"Biological sample," as that term is used herein, means a sample obtained from an animal that can be used to assess the presence, absence and/or level, of a nucleic acid. Such a sample includes, but is not limited to, a blood sample, a semen sample, a hair sample, a nail sample, a brain sample, a kidney sample, an intestinal tissue sample, a tongue tissue sample, a heart tissue sample, a mammary gland tissue sample, a lung tissue sample, an adipose tissue sample, a muscle tissue sample, and any sample obtained from an animal that can be assayed for the presence or absence of a nucleic acid.

"Clinical Laboratory" means a facility for the biological, microbiological, serological, chemical, immunohematological, hematological, biophysical, cytological, pathological, or other examination of materials derived from the human body for the purpose of providing information for the diagnosis, prevention, or treatment of any disease or impairment of, or the assessment of the health of, human beings. These examinations also include procedures to determine, measure, or otherwise describe the presence or absence of various substances or organisms in the body. Facilities only collecting or preparing specimens (or both) or only serving as a mailing service and not performing testing are not considered laboratories.

"Clinical laboratory test" and "clinical test," as these terms are used interchangeably herein, essentially follow the CLIA '88 definition: Procedures to determine, measure, or otherwise describe the presence or absence of various substances or organisms in the body through examination of materials derived from the human body for the purpose of providing information for the diagnosis, prevention, or treatment of any disease or impairment of, or the assessment of the health of, human beings.

By "complementary to a portion or all of the nucleic acid encoding a target sequence" is meant a sequence of nucleic acid which does not encode a target sequence. Rather, the sequence which is being expressed in the cells is identical to the non-coding strand of the nucleic acid encoding a target sequence.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 500, even more preferably, at least about 500 nucleotides to about 800 nucleotides, yet even more preferably, at least about 800 to about 1000, even more preferably, at least about 1000 nucleotides to about 1200 nucleotides, yet even more preferably, at least about 1200 to about 1500, and most preferably, the nucleic acid fragment will be greater than about 1500 nucleotides in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example, at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See the National Center for Biotechnology Information world wide web site.

The percent identity between two sequences can be determined using techniques similar to those described above, with or without allowing gaps. In calculating percent identity, typically exact matches are counted.

By the term "intronic border," as the term is used herein, is meant a region of from about 30 to 100 basepairs near the 5' and 3' termini of an exon.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the mouse proteins described herein are within the scope of the invention. Nucleic acid molecules corresponding to natural allelic variants and homologs of a cDNA of the invention can be isolated based on their identity to mouse nucleic acid molecules using the mouse cDNAs, or a portion thereof, as a hybridization probe according to standard hybridization techniques under stringent hybridization conditions.

As used herein, an "instructional material" includes a publication, a recording, a diagram, or any other medium of expression which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

"Marker gene", as used herein, encompasses a gene in an expression vector that is situated close to target DNA whereby expression of the marker gene indicates the insertion of the target DNA in the expression vector.

The term "nucleic acid construct," as used herein, encompasses DNA and RNA sequences encoding the particular gene or gene fragment desired, whether obtained by genomic or synthetic methods.

By the term "nucleic acid preparation" is meant that a DNA or RNA fragment of interest, or equivalently, the base sequence for which the patient sample is being assayed, is obtained using standard molecular biology techniques and protocols knowledgeable to one skilled in the art. Such techniques will not be repeated herein but are set forth in detail in Sambrook et al. (1989, In: Molecular Cloning-A Laboratory Manual, $2^{nd}$ edition, Cold Spring Harbor Laboratory Press, New York), the disclosure of which is hereby incorporated by reference. A DNA fragment of interest may be custom-synthesized using a variety of commercially available methods and instruments known to one skilled in the art.

"Nucleic acid reference standard," as the term is used herein, encompasses all nucleic acid-based, i.e., comprising a nucleic acid where the nucleic acid is detected based on its sequence, quality control standards comprising a nucleic acid (e.g., RNA and DNA) comprising a known sequence useful in a nucleic acid test. The reference standard contains nucleic acid sequences useful to validate or standardize a nucleic acid test. The reference standard is used to evaluate the ability of the test to detect or measure one or more specific nucleic acid sequences and/or to accurately indicate the absence of the specific nucleic acid sequence(s).

A reference standard can be, but need not be, bound or encapsulated with a microparticulate binding agent. Indeed, some of the current proficiency standards are not bound or encapsulated; rather, these standards enter the assay to be validated at the amplification step, thereby by-passing the extraction step(s) of the assay. Therefore, the construct of the invention can serve as a nucleic acid reference standard without being bound or encapsulated. The construct is very useful suspended in a solution or lyophilized in a vial and can be used as a control for an extracted DNA sample. However, wherever it is desired that the construct serve as a control which can assess the extraction step also, the construct of the invention can be bound or encapsulated as well-known in the art.

A "control," as the term is used herein, is a substance of known analyte(s) (e.g., a nucleic acid comprising a known sequence) which, when tested alongside substances of unknown analytes, i.e., a patient sample, is used to assess the accuracy and precision of the test.

By the terms "nucleic acid test", "nucleic acid assay," or "molecular tests," is meant procedures to determine, measure, or otherwise describe the presence or absence of various nucleic acids and nucleic acid sequences through examination of materials derived from the environment, from organisms, from an animal or from a human body.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574). Similarly, horseradish peroxidase, alkaline phosphatase, and green fluorescent protein genes are detectable markers that are encompassed in the invention.

A "restriction site" is a portion of a double-stranded nucleic acid which is recognized by a restriction endonuclease. An extensive list of known restriction sites is available to the public on the world wide web at the New England Biolabs website, which site has been reviewed by Roberts et al. (2001, Nucleic Acids Res. 29:268–269).

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, N.Y.).

By the term "each fragment specifies a component associated with at least one of a disease state, an environmental condition, or a biological organism," as used herein, is meant that the fragment comprises a nucleic acid sequence associated with a disease state (e.g., tuberculosis, cystic fibrosis, hematochromatosis, a blood clotting disorder, hepatitis C, and the like), an environmental condition (e.g., pathogenic microorganisms such as Cryptosporidium and Giardia being present in a water sample), or a biological organism (e.g., a marker used in molecular forensics, strain-typing of *Mycoplasma tuberculosis*, a parvovirus B19 nucleic acid, and the like). The component associated with the particular feature, i.e., the disease state, environmental condition, and biological organism, can be any nucleic acid specifically associated with the feature. The fragment can have a wild type or mutant sequence and can be related to the presence of disease or to the absence of disease.

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

"Performance characteristic" means a property of a test that is used to describe its quality, e.g., accuracy, precision, analytical sensitivity, analytical specificity, reportable range, reference range, etc.

"Performance specification" means a value or range of values for a performance characteristic, established or verified by the laboratory, that is used to describe the quality of patient test results.

"Referee laboratory" means a laboratory currently in compliance with applicable CLIA requirements, that has had a record of satisfactory proficiency testing performance for all testing events for at least one year for a specific test, analyte, subspecialty, or specialty and has been designated by an HHS approved proficiency testing program as a referee laboratory for analyzing proficiency testing specimens for the purpose of determining the correct response for the specimens in a testing event for that specific test, analyte, subspecialty, or specialty.

"Reference range" means the range of test values expected for a designated population of individuals, e.g., 95 percent of individuals that are presumed to be healthy (or normal).

"Sample" in proficiency testing means the material contained in a vial, on a slide, or other unit that contains material to be tested by proficiency testing program participants.

A fragment "specifies a component associated with" a disease state, an environmental condition and/or a biological organism when the fragment comprises a nucleic acid associated with or diagnostic for the disease state, environmental condition or biological organism, which can be used to detect such disease state, environmental condition or biological organism in a test sample using a nucleic acid assay.

"Reference nucleic acid" encompasses all DNA and RNA used for validation, standardization, quality control, and quality assurance purposes in molecular screening and diagnostic assays in manual, automated, kit and non-kit forms, and includes standards, controls, and calibrators.

The term "target nucleic acid," as used herein, encompasses DNA and RNA having a base sequence containing a target sequence to be analyzed in the test specimen.

By the term "vector" as used herein, is meant any plasmid or virus encoding an exogenous nucleic acid and/or comprising a fragment where the fragment comprises a target nucleic acid sequence to be introduced into a cell. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the control DNA construct to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Description

The invention relates to a method of designing and constructing synthetic control DNA constructs for the production of a comprehensive controls series useful for quality assurance in the diagnostic detection of complex genetic diseases such as, but not limited to, Cystic Fibrosis. In contrast to the current practice of using patient-derived biological material as a control, the present invention provides a renewable source of control material adaptable to represent any of a large number of mutations, including rarer mutations that are often unavailable from patient sources.

Further, the nucleic acid constructs of the invention represent a vast improvement over prior art constructs which require that separate constructs be used to assay whether a particular nucleic acid of interest is present or absent in a sample being queried in that the constructs of the invention comprise multiple nucleic acids of interest thus vastly reducing the number of constructs that must be used in a nucleic acid assay to assay a complex sample for multiple nucleic acids of interest. This reduces the probability of error in sample manipulations, the amount of materials required, and in time since a single construct of the invention provides a control for a variety of nucleic acids without need of using multiple, separate nucleic acid controls.

Since some genes are very large, the CFTR gene for example is 230 kilobases (kb) long, the vector of choice for cloning such a fragment would ordinarily be a yeast artificial chromosome (YAC) (Sambrook et al., 1989, In: Molecular Cloning: A Laboratory Manual, Cold Spring Harbor Laboratory, New York). However, YACs are often unstable and the yield of cloned DNA per cell is low (Strachan et al., 1996, In: Human molecular genetics, BIOS Scientific Publishers Limited), thus, the present invention overcomes limitations prior art methods by circumventing the use of YAC vectors; rather, the present invention relates to a novel approach of ligating selected DNA fragments through unique restriction enzyme sites. The design of the ligations enables construction of a cloned DNA control construct comprising any and all the significant DNA fragments for a disease or test.

The approach is exemplified by, but not limited to, the design and production of a DNA control construct of approximately 6.5 kb to 10 kb representing all 27 CFTR exons. The ligation scheme disclosed herein allows insertion of the DNA control construct into the pGEM®-T (Promega, Madison, Wis.) plasmid vector system, which is extremely stable and which is amenable to encapsulation to more closely resemble the biological starting material such as cells or virus particles.

The constructs are engineered to produce DNA controls in several configurations that represent various genotypes and combinations of genotypes observed in a population. The invention is exemplified, but not limited to, three controls, each containing two DNA fragments, exons 10 and 11 and their intronic borders, from the CFTR gene. In addition to the wild type control, mutant control vectors were constructed, each carrying distinct mutations, deltaF508 and deltaI507. Final reference products were made by transforming Top10F' *E. coli* with the constructs, growing the clone, and subsequently extracting the vector and suspending it in suitable medium.

The data disclosed herein demonstrate design and production of constructs that allow for modifications in the future. A set of vectors was developed that permit the easy addition of fragments to produce a series of reference products for nucleic acid testing. Following the creation of stable *E. coli* cell banks that carried these vectors, the wild-type vector and two mutant vectors were assessed in current cystic fibrosis assays. Identification of an efficient system of fragment ligation and mutation while retaining the desired sequence demonstrated the feasibility of the synthetic construct approach. Thus, the data disclosed herein demonstrate a novel, innovative approach to production of a comprehensive series of reference materials for CF mutation detection diagnostic assays and for other nucleic acid assays.

I. Control DNA construct

The invention includes an isolated control DNA construct. The construct comprises a vector, which allows the construct, and nucleic acids contained therein, to be replicated and/or expressed in a cell. One skilled in the art would appreciate that there are a wide plethora of vectors for the expression and replication of nucleic acids. Such vectors are described in, e.g., Sambrook et al., supra, and Ausubel et al., supra, and the choice of vector used in the invention is not limited, but encompasses any vector known in the art and/or to be developed in the future.

Further, the invention is not limited to the type of cell comprising the construct. Rather, any cell, including prokaryotic and eukaryotic, can be used to propagate the construct of the invention.

The construct comprises two or more nucleic acid fragments where the fragments comprise one or more target sequences of interest that can be detected using molecular probes. The two or more fragments are ligated into the vector in such a way that they can be ligated together in a preferred 5' to 3' order. This is accomplished in that each fragment to be ligated together comprises a unique restriction site at both 3' and 5' ends and where each restriction site is complimentary with the restriction site of an adjacent, or flanking, nucleic acid. That is, the 5' end of the first, i.e., the 5' most, fragment is covalently linked to the 3' end of the vector via a unique restriction site that is not present anywhere else in the final construct once all of the fragments have been ligated in.

Unique restriction sites can be designed by selecting restriction sites that naturally occur in the fragments to be ligated into the construct. Alternatively, the restriction sites can be generated by methods known in the art and/or to be developed in the future, including, but not limited to, restriction sites created by including the pertinent sequence in the primer tails used to produce the proper restriction sequences at the ends of each fragment, and methods such as described in Gal et al., 1999, Mol. Gen. Genet. 260:569–573). Thus, the skilled artisan, armed with the teachings provided herein, would appreciate that the restriction site can be easily generated to provide unique sites between the fragments and the vector and between the individual fragments where the nucleic acid sequence in the fragment is known such that the restriction site will not be present either within the fragment or elsewhere in the construct.

The skilled artisan would appreciate, based upon the disclosure provided herein, that the invention includes a wide plethora of restriction sites that do not cleave the pGEM plasmid vector such as, but not limited to, BssH II, Csp45 I, Age I, AccB7, IAcc III, Acc65 I, AflII, AscI, AvaI, Avr II, BalI, BamH I, BbeI, BbrP I, BbsI, Bcl I, BglII, BlpI, Bpu1 102 I, BsaB I, BsaM I, BsmI, BsrBR I, BsrG I, Bst1 107 I, Bst98 I, BstE II, Bsu36 I, ClaI, CspI, DraII, Eco47 III, Eco72 I, Eco81 I, EcoN I, EcoR I, EheI, FseI, Hind III, HpaI, I- PpoI, KasI, KpnI, NarI, NheI, NruI, Pac I, PflM I, PinA I, PmeI, PmlI, PpuM I, PshA I, Psp5 II, PspA I, RsrII, SgfI (k), SgrA I, SmaI, SnaB I, SplI, SrfI, StuI, SwaI, Tth111 I, XbaI, XcmI, XhoI, XmaI, and the like. The only limitation on the choice of restriction site is that the restriction site cannot be present elsewhere in the construct. Other than that, any restriction site, known in the art or to be developed, is encompassed in the invention. That is, the skilled artisan would appreciate, based upon the disclosure provided herein, that each restriction site used to insert and excise the fragments comprising the target nucleic acid sequence of interest must be unique in that the restriction site cannot occur at any other position in the construct.

A wide variety of restriction enzymes, which cleave nucleic acids at a wide plethora of restriction sites, is available and an extensive list of the restriction sites is available to the public at the New England Biolabs website. Further, this internet web site and the wide plethora of available restriction sites was reviewed recently by Roberts et al. (2001, Nucleic Acids Res.29:268–269). Thus, the skilled artisan, armed with the teachings provided herein, could easily determine which restriction sites to use for any given nucleic acid fragment to be inserted into the construct, and/or any mutants or variants thereof. Having a unique restriction site at each end of each fragment allows the fragments to be individually excised. The fragment can then be manipulated by, for instance, by mutagenesis to introduce a mutation of interest into the fragment, or replaced with an entirely different fragment comprising a sequence of interest. Thus, cutting with any one of the unique restriction enzymes linearizes the construct and restriction at a second restriction site not present elsewhere in the construct excises a single fragment. The construct can be re-ligated by modifying the 5' and 3' ends thereof to generate complimentary "sticky" ends. Alternatively, a new fragment, or a modified version of the previously excised fragment, can be inserted by matching the unique restriction sites at each end of the fragment such that the 5' end of the fragment to be replaced/reintroduced into the construct, is complimentary with the 3' end of the linearized construct, and, likewise, the 3' end of the fragment being introduced/reintroduced into the construct is complimentary with the 5' end of the linearized construct.

The skilled artisan would appreciate, based upon the disclosure provided herein, the wide plethora of arrangements that are encompassed by the invention. That is, virtually any fragment comprising a nucleic acid sequence of interest can be introduced into the construct using the methods disclosed herein and those well-known in the art of recombinant nucleic acid technology. Thus, the invention encompasses a nucleic reference standard comprising a wide plethora of target nucleic acids, including, but not limited to, a methyltetrahydrofolate reductase gene, a beta cystathionase synthetase nucleic acid, nucleic acid related to coagulation factors including factor II, factor VII, factor VIII, and factor IX, a nucleic acid associated with prothrombin, nucleic acid containing translocations related to hematologic disease including a BCR/abl nucleic acid, and other nucleic acids related to the genetic diseases as listed in the GENETESTS® database maintained by Hanson et al. That is, many nucleic acid sequences associated with a disease, disorder or condition are described at the genetests.org web site, and the web site provides an extensive list of genetic diseases wherein a mutation has been identified that is associated with the disease, while the number of genetic diseases identified which are correlated to a known mutation (s) is expanding every day.

Therefore, the following discussion, while illustrative, should not be construed to limit the invention in any way. More specifically, the fragments can: comprise exons, introns, or both, of a single gene (e.g., at least one exon of a CFTR gene; BRCA1 and BRCA2 genes); each fragment can comprise a variety of sequences of interest; each derived from various organisms (e.g., the fragments can be from various pathogens associated with a single disease or disorder for diagnostic purposes such as, but not limited to, a *Mycobacterium tuberculosis* genome; a *Chlamydia trachomatis* genome; a parvovirus B19 nucleic acid; an HIV genome; a hepatitis C virus genome, or fragments of these); fragments of various nucleic acids the products of which are associated with a disease, disorder or condition (e.g., for a disease, disorder or condition associated with abnormal clotting, the construct can comprise a fragment of a gene encoding a common factor V mutation and a fragment comprising a prothrombin 20210 gene fragment comprising a prothrombin disease-related mutation; and a nucleic acid associated with hereditary hemochromatosis, and a lipoprotein lipase gene); a series of fragments useful for diagnosis or strain-typing related to tuberculosis; fragments comprising various pathogens associated with a disease, disorder or condition such as those pathogenic organisms that are known to colonize cystic fibrosis patients; various nucleic acids for identifying and detecting organisms present in an environmental sample of interest (e.g., a water sample can be assayed for the presence or absence of various microorganisms such as, but not limited to, Cryptosporidium, Giardia, and the like); and the like.

More specifically, each fragment specifies a component associated with at least one of a disease state, an environmental condition, or a biological organism. That is, one skilled in the art would understand, based upon the disclosure provided herein, that the construct of the invention comprises more than one marker that is associated with a feature which is indicative of the absence or presence of a disease state, an environmental condition relating to the presence or absence of an organism in the environment, and/or a biological organism. Thus, as more fully set forth elsewhere herein, the construct can be designed to include multiple fragments such that a composite array of markers associated with a particular disease state, environmental feature, or biological organism is produced which can be used as a control for a nucleic acid assay useful for assessing the presence or absence of the disease state, environmental feature, or biological organism. For instance, as exemplified herein, the construct can comprise various fragments comprising several exons of the CFTR gene such that the construct comprises several mutations and/or variants associated with CF. Similarly, a construct can comprise a nucleic acid associated with human immunodeficiency virus along with fragments comprising various nucleic acids associated with pathogens that are typically associated with opportunistic infections of immunosuppressed individuals. Moreover, a construct can comprise not only various mutations and variations associated with CF, but can further comprise nucleic acids that are specific markers for the pathogens that typically infect CF-patients such as, but not limited to *Pseudomonas aureginosa*. In addition, the invention includes a construct comprising various fragments comprising nucleic acids associated with an environmental feature such as, but not limited to, detection of pathogenic organisms present in drinking water and other water samples. The construct can comprise various nucleic acids associated with various pathogens such as cryptosporidium and giardia, among others. The construct can comprise several nucleic acid sequences associated with human genetic markers such that the construct can be used as a control in forensic nucleic acid assays such as those used to establish paternity and those used in criminal investigations such as to establish culpability (e.g., establishing whether the defendant is guilty or not based on a semen, hair, nail clipping, and skin sample). Therefore, an important improvement over the prior art is that a single construct can serve as control to assess the presence or absence of several nucleic acids of interest, which nucleic acids are related since they are associated with a disease state, an environmental condition, and a biological organism.

However, although multiple nucleic acids associated with a disease state, environmental condition, and or a biological organism, the skilled artisan would appreciate, based upon the disclosure provided herein, that the construct can be used to represent any or all of the nucleic acid sequences which are present in the construct or the construct can be used to represent any one of the sequences and need not be assayed for all at one time in a single nucleic acid assay. Nonetheless, the skilled artisan would appreciate that the construct of the invention provides a control that can be used to validate a nucleic acid test for the presence or absence of a compilation of myriad nucleic acid sequences each of which is associated with a disease state, an environmental condition, or a biological organism. Thus, the construct provides a single DNA control thereby avoiding having to perform several nucleic acid assays thus reducing the probability of sample handling errors and providing a substantial savings in terms of reagent costs and time associated with sample processing, in that a single control can be used instead of having to use multiple controls. However, one skilled in the art would appreciate, based upon the disclosure provided herein, that although at least two fragments are present in the construct and each fragment specifies a component associated with at least one of a disease state, an environmental condition, or a biological organism, and each fragment comprises a different component, not all components need be detected by a single nucleic acid assay. Indeed, the construct can comprise control sequences, such as wild type or other sequences that would not be expected to be in a sample being queried, such that not all components present in the construct need be detected and some maybe should not be detected if the nucleic acid assay is performed properly. The skilled artisan would appreciate the many variations possible and encompassed in the present invention.

In sum, the skilled artisan, based upon the disclosure provided herein, could readily design a construct of the invention comprising nucleic acid sequences of interest where the end of one fragment is complimentary with the end of the adjacent restriction site on the flanking fragment. The method comprises designing the sequence of interest and the flanking fragment to have a common restriction enzyme site at the location where they will be joined. Digesting the two segments with the restriction enzyme will then produce the desired complimentary ends, known in the art as "sticky ends".

One skilled in the art would appreciate, based on the disclosure provided herein, that the invention includes a construct comprising all or fewer of the 27 exons comprising the CFTR gene. That is, the CFTR gene encompasses about 230 kb and comprises several exons and introns. The skilled artisan would appreciate, based upon the disclosure provided herein, that the invention encompasses a construct comprising preferably, one CFTR exon, more preferably about 3 CFTR exons, even more preferably, about 5 exons, yet more preferably, about 8 exons, more preferably, 15 CFTR exons, even more preferably, about 20 CFTR exons, yet more preferably, about 25 CFTR exons, and most preferably, about 27 CFTR exons. Preferably, a reference material for any genetic test includes all of the exon and intronic segments that are tested or that affect the test result. The cystic fibrosis gene has over 900 known mutations. There are important mutations in all of the CFTR exons. The reference CFTR DNA preferably includes all 27 of the CFTR exons and their intronic borders. The most common disease related CFTR mutations seen in the United States occur in exons 10 and 11. A reference CFTR DNA would, at a minimum contain these two exons.

One skilled in the art would appreciate, based upon the disclosure provided herein, that the fragments can comprise a wild type sequence of a gene of interest and as many mutations and variations thereof as is desired. Without wishing to be bound by any particular embodiment, the invention includes a construct comprising a CFTR exon 10 (SEQ ID NO:9), wherein the exon 10 can comprise one or more mutations relative to the wild type exon 10 (e.g., a G480C mutation, a D1507 mutation, a DF508 mutation, and the like), and or at least one or more polymorphisms (e.g., a F508C polymorphism, a 1507V polymorphism, a 1506V polymorphism, and the like). Similarly, the invention includes a construct comprising a CFTR exon 11 (SEQ ID NO: 10), wherein the exon 11 can comprise one or more mutations relative to the wild type exon 11 (e.g., a G542X mutation, a G551D mutation, a R553X mutation, a A559T mutation, a R560T mutation, and the like), and or at least one or more polymorphisms. The invention also encompasses fragments comprising a mutation in an intron, such as, but not limited to, a 1717-1 G to A mutation in intron 10.

The routineer would appreciate that the mutation and/or polymorphism can be present on the same fragment or on separate fragments within the construct.

Preferably, the construct comprises exon 10, exon 11, or both. The exons can be ordered in any order or orientation within the construct such that a fragment comprising CFTR exon 10 can be 5' to a fragment comprising CFTR exon 11, or vice versa. The construct also may contain mutant and wild type sequences of the same exon ligated together and with mutant and wild type sequences of other exons. For example a CFTR wild type exon 10 ligated to a CFTR mutant exon 10 ligated to a CFTR wild type exon 11 and etc. The order of the fragments is not important and the invention encompasses any arrangement of the fragments within the construct. However, the ligation design of the invention allows the fragments to be ordered if desired. For example, it may be optimal for manufacturing, or for an assay not yet developed, to order the CFTR construct so that the 5' fragment is exon 1 and the 3' fragment is exon 27.

In addition to the mutations and polymorphisms disclosed previously herein, the present invention encompasses any mutation, polymorphism, or both, of the CFTR gene such as, but not limited to, those provided in the list set forth at the Cystic Fibrosis Mutation Data Base web site, which site is maintained by Lap-Chee Tsui et al.

The invention includes a construct wherein a fragment comprises a reporter gene as that term is defined and used herein. The skilled artisan would understand, based upon the disclosure provided herein, that the invention encompasses that, where several reporter genes are included in the construct, the reporter genes can be on a single fragment flanked by unique restriction sites or the reporter genes can be present on various fragments. The skilled artisan would further appreciate, based on the disclosure provided herein, that a wide plethora of reporter genes, including genes encoding resistance to various compounds such as ampicillin and kanamycin, to name a few, as well as reporter genes such as, but not limited to, horse radish peroxidase, alkaline phosphatase, chloramphenicol transferase, and green fluorescence protein, are encompassed in the invention.

One skilled in the art would appreciate, based upon the disclosure provided herein, that the vector, as that term is used and defined elsewhere herein, includes, and is not limited to, a plasmid, a virus, a bacteriophage, a cosmid, artificial chromosomes or other system that can self-replicate when incorporated into a host system. Vectors and types of cloning systems are described in Sambrook et al., supra.

The control DNA construct can be used in any nucleic acid assay based on detecting the presence or absence of a nucleic acid sequence. Such assays include, but are not limited to, Southern blotting, dot blots, northern blotting, and the like, to detect the presence or absence of a nucleic acid of interest. The skilled artisan would appreciate, based upon the disclosure provided herein, that the invention includes use of the construct according to methods for producing stable nucleic acid control standards for assessing the proper sample handling in nucleic acid assays. Such methods include, but are not limited to, methods where the construct is bound with a binding agent rendering the construct stable for use in such assays as described in, e.g., U.S. Pat. Nos. 5,994,078, and 6,013,434, and 5,677,124.

II. Methods

A. Method of Producing a Control DNA Construct

The invention includes a method of producing a control DNA construct. The method comprises covalently linking the 3'- end of a linearized vector with the 5'- end of a nucleic acid fragment via a restriction site not present elsewhere in the construct. The 5' end of the linearized vector is also linked to the 3' end of another fragment via another restriction site not present elsewhere in the construct. Further, the 3' end of the 5'-most nucleic acid fragment can be linked with the 5' end of the 3'-most fragment via a restriction site not present elsewhere in the construct. Also, several fragments can be inserted into the construct where the 5'-end of each fragment is linked with the 3'-end of another fragment via a unique restriction site not present elsewhere in the construct. Thus, the construct is circularized upon addition of the last fragment comprising a 5'-end complimentary to the 3'-end of the 5' most fragment which fragment also comprises a 3'-end complimentary to the 5'-end of the 3' most fragment.

As discussed elsewhere previously herein, the fragments can comprise a wide plethora of nucleic acid sequences and the fragments can be removed and either mutated using standard mutagenesis techniques to produce mutant nucleic acid sequences of interest and the fragment is then re-ligated into the construct, and/or the fragment can be excised by cleaving the unique restriction sites flanking the fragment and a different fragment can be inserted into the construct where the new fragment comprises the requisite unique restriction sites at both ends of the fragment. The whole construct or any multiple fragment part can also be removed and mutated using standard mutagenesis techniques to produce mutant nucleic acid sequences of interest and the fragment is then re-ligated into the original construct or into a new construct.

One skilled in the art would appreciate, based upon the disclosure provided herein, that the fragment can be produced by a variety of methods, including, but not limited to chemical synthesis, cleavage of a genomic sequence, production of a complementary DNA sequence (e.g., by reverse transcription of a mRNA molecule), and in vitro amplification of a DNA fragment. Thus, the invention is not limited as to how the fragment is obtained.

B. Method of Assessing the Accuracy of a Nucleic Acid Based Assay

The invention includes a method of assessing the presence or absence of a nucleic acid of interest in a sample. The method comprises processing a control DNA construct of the invention, either in parallel or at a different time, or, more preferably, in parallel with a sample being assessed in a nucleic acid assay.

One skilled in the art would appreciate, based upon the disclosure provided herein, that the particular method used to perform the nucleic acid assay, such as the methods described in Sambrook et al., supra, and Ausubel et al., supra, is not crucial to practicing the present invention. What is important, among other things, is that the construct comprise a fragment where the fragment specifies a component associated with at least one of a disease state, an environmental condition, or a biological organism. Thus, unlike prior art constructs useful for identifying whether one or just a few nucleic acid sequences of interest can be detected by a nucleic acid assay, the methods herein disclose a novel construct, and novel uses therefore, comprising multiple nucleic acids comprising a feature of a disease state, environmental condition, and a biological organism such that the construct of the invention allows multiple nucleic acids to be used as a control to determine whether the test being validated can accurately detect a variety of nucleic acid sequences, or a variety of tests can detect multiple nucleic acids contained in one construct, thus simplifying the validation of one or more assays and ensuring the accuracy and reliability of those assays.

III. Kits

The invention includes a kit for producing a control DNA construct. Although exemplary kits are described below, the contents of other useful kits will be apparent to the skilled artisan in light of the present disclosure. Each of these kits is included within the invention.

The kit comprises a vector and at least two nucleic acid fragments. The vector comprises at least two restriction sites that do not appear elsewhere in the construct and when cleaved by the restriction endonucleases specific for those sites, the vector comprises a unique restriction site at either end. Further, each fragment comprises a restriction site at each end wherein the restriction site does not appear elsewhere in the construct and it is complimentary with a restriction site at the end of another fragment or with a restriction site present at the end of the vector.

Moreover, the kit comprises an applicator and an instructional material for the use of the kit. These instructions simply embody the examples provided herein.

The kit further comprises a restriction endonuclease specific for the restriction site.

The invention is further described in detail by reference to the following experimental examples. These examples are provided for purposes of illustration only, and are not intended to be limiting unless otherwise specified. Thus, the invention should in no way be construed to be limited to the following examples, but rather, should be construed to encompass any and all variations which become evident as a result of the teaching provided herein.

EXAMPLE 1

Construction of DNA Cassette Clones

The experiments presented in this example may be summarized as follows.

The data disclosed herein demonstrate construction of clones comprising CFTR exons 10 and 11 cassettes.

The Materials and Methods used in the experiments presented in this example are now described.

PCR Amplification of CFTR Exons 10 and 11.

The exact target sequences of CFTR exons 10 and 11 were identified from published data with emphasis that the control products contain sufficient sequence that will be required in emerging CF testing methodologies. The sequence of all 27 CFTR exons was obtained from GenBank. Comparisons were made between older entries of the individual exons (Zielenski, et al., 1991, Ref Genomics 10: 214–228 and GenBank Accession Nos. M55106–M55131) and the newer entries of BAC clones 068P20 GenBank Accession No. AC000111, and 133K23 GenBank Accession No. AC000061, and exact intronic borders were determined.

Figure 2:
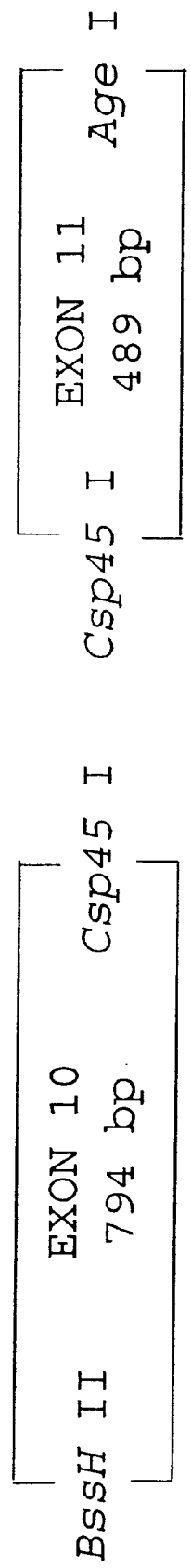
FIG. 2 is a diagram of the restriction enzyme scheme used for design of the exon 10 and 11 cassettes.

Primers were selected such that the widely published Zielinski sequences would be included within the cassettes. BssH II and Csp45 I restriction enzyme sites were incorporated on the 5' and 3' ends, respectively, of the exon 10 cassette (FIG. 2). These restriction sites do not occur in the entire target CFTR sequence, thus ensuring that these restriction enzyme choices will not interfere with inclusion of other cassettes from the CFTR into a larger construct.

The exon 11 cassette was amplified with primers containing Csp45 I and Age 1 sites. DNA cassettes containing CFTR exon 10 and CFTR exon 11 were synthesized using primers: CFEX10F1: 5'AACAGC<u>G</u>C<u>G</u>CGACACAGA 3' (SEQ ID NO:1), CFEX10R1: 5'CCATTTC<u>G</u>AAAAATGCATTTATTGTGA3' (SEQ ID NO:2), and CFEX11F1: 5'GCATT<u>C</u>GAAATAATGGAGATGCA3' (SEQ ID NO:3); and CFEX11R1: 5'CAA<u>A</u>C<u>C</u>G<u>GTACACTGACACCAA</u>3' (SEQ ID NO:4). The underlined bases in the primer sequences denote the modifications introduced to produce the selected restriction enzyme sites.

The exon 11 cassette was PCR-amplified using CLONTECH's Advantage™ HF 2 Polymerase Mix per the manufacturer's instructions (Clontech Laboratories, Inc., Palo Alto, Calif.). Fifty microliter PCR reactions were run according to standard protocol. Briefly, PCR cycling conditions were: 94° C. for 5 minutes, 32 cycles of 94° C. for 15 seconds, 63° C. for 15 seconds, 68° C. for 20 seconds, 2 holds of 68° C. for 5 minutes each, and a 4° C. final hold.

Exon 10 cassette was amplified with AmpliTaq Gold™ per the manufacturer's instructions. PCR cycling conditions were: 95° C. for 10 minutes, 31 cycles of 94° C. for 30 seconds, 64° C. for 30 seconds, 72° C. for 35 seconds, hold of 72° C. for 10 minutes, and final hold at 4° C. The exon 10 cassette product yield was somewhat weak, so 6 PCR reactions were pooled. Cassette amplicons were purified by absorption on to a silica membrane at pH 5, followed by buffered alcohol wash and elution at pH 8.5. Specific amplification products were visualized on 6% polyacrylamide gel using ethidium bromide staining and ultraviolet illumination. The final yield was approximately 2.5 µg of exon 10 cassette at a concentration of 50 ng/µl and 4.9 µg of exon 11 cassette at a concentration of 98 ng/µl.

The nucleic acid sequence of each cassette amplicon was determined using cycle sequencing with BigDye Terminators (Applied Biosystems, Inc., Foster City, Calif.), using forward and reverse PCR primers. The forward and reverse primers were the same as those disclosed previously elsewhere herein which were used for amplification of the cassette exons 10 and 11. Analysis was performed on an ABI Prism 310 (Applied Biosystems, Inc., Foster City, Calif.).

Exon 11 was found to be wild type and exon 10 was wild type except for an A to G substitution on 1 allele at nucleotide 1080 relative to the sequence published in GenBank Accession L49160. This nucleotide substitution is described by Kerem et al. (1990, Proc. Natl. Acad. Sci. USA 87:8447–8451), as a benign polymorphism at nucleotide 1540, using nucleotide numbering systems of Riordan et al., 1989, Science 245:1066, and GenBank Accession NM_000492.

Insertion of CFTR Exons 10 and 11 into Expression Vectors

The Exon 10 and Exon 11 cassette amplicons, were A-tailed using the Taq polymerase and were ligated individually into pGEM-T plasmids using standard cloning methods. Exon 10 and Exon 11 cassettes were also were ligated together, after digestion, via their common restriction site, Csp45 I (TT*CGAA) (Promega Corp., Madison, Wis.), and were ligated into pGEM-T plasmid.

Ligation of individual cassettes into pGEM-T was accomplished by mixing 5 µl of 2× Buffer (60 mM Tris-HCl, pH 7.8, 20 mM MgCl$_2$, 20 mM DTT, 2 mM ATP and 10% polyethylene glycol, PEG), 1 µl of pGEM-T open vector (50 ng/µl), 31 µl Exon 10 or Exon 11 amplicon, and 1 µl T4 Ligase (4.0 Weiss units/µl) and incubating the mixture overnight at 4° C. The ligation product (10 µl) was precipitated by mixing with 1 µl glycogen, 5 µl of 7.5 M ammonium acetate, and 30 µl of 100% ethanol and incubation at −70° C. for 10 minutes. The precipitate was separated by centrifugation at 12,000×g and was washed with 50 µl of 70% ethanol. After drying the sample was dissolved in 10 µl of nuclease-free DI water.

Transformation of Bacterial Cells with CFTR Exons 10 and 11 Clones.

Electroporation was performed as described below with the Bio-rad GenePulser™, followed by 1 hour incubation in S.O.C. medium (Life Technologies, Inc., Rockville, Md.) and plating on LB/ampicillin plates.

Cuvettes were chilled on ice. Electrocompetent cells Invitrogen TOP10F' were thawed on ice. One µl of plasmid DNA was added to 40 µl cell suspension, gently mixed and incubated on ice for 1–2 minutes. The cell/plasmid DNA suspension was transferred to the cold cuvette and electroporation was conducted at 1.6 kV, 25 µf, 200 ohms, with a pulse of 4–5 mseconds. 960 µl S.O.C. medium was added immediately to cuvette. The cells (in SOC) were transferred immediately to a test tube and incubated 1 hour at 37° C. with agitation. Electroporated cells were streaked on plates with selective L/B ampicillin media and incubated overnight at 37° C.

Isolation of CFTR Exon 10 and 11 Cloned DNA.

White colonies were picked and cultured in LB/ampicillin medium, cells were isolated by centrifugation and resuspended in a 50 mM Tris-HCl, pH 7.5, 10 mM EDTA solution. Plasmid from the cells was purified and separated using Promega Wizard®Plus Minipreps DNA Purification System. In this protocol cells were lysed by adding a volume of Cell Lysis Solution (0.2 M NaOH in 1% SDS (sodium dodecyl sulfate)) and inverting the tube 4 times. The solution was neutralized with 300 µl of 1.32M KOAc (potassium acetate), pH 4.8 and debris removed by centrifugation. Plasmid was then separated by absorption on to a filter bed of silica and silica fibers in 4.2 M guanidine HCl. The plasmid was washed with 2 mL of wash solution (80 mM potassium acetate, 8.3 mM Tris-HCl, pH 7.5, 40 uM EDTA, 55% ethanol) and then eluted with 50 µl of nuclease free water. Plasmid from three different cultures were sequenced in both directions with plasmid based pUC M13 primers using ABI PRISM BigDye Terminator Cycle Sequencing Reaction Mix. 20 µl reactions were cycled as follows: 25 cycles of 96° C. for 10 seconds, 50° C. for 5 seconds, 60° C. for 4 minutes. The reactions were purified by ethanol/sodium acetate and analyzed on the ABI PRISM 310. DNA sequence exactly matched that of the original cassette amplicon in all three cases. Three ml of cell suspension from one of the positive clones was grown overnight and then mixed with 2 ml sterile glycerol and aliquots frozen at −70° C.

EXAMPLE 2

Construction of Clones Containing Restriction Site-Linked CFTR Exons 10 and 11.

The experiments presented in this example may be summarized as follows.

The data disclosed herein describe the construction of clones containing restriction site-linked CFTR exons 10 and 11 cassettes.

The Materials and Methods used in the experiments presented in this example are now described.

PCR Amplification of CFTR Exon 10 and 11 Cassettes.

Exon 10 and exon 11 cassettes were amplified in fifty microliter PCR reactions using primers and reagents as describe above. The amplicon was purified using the Qiagen Qiaquick® DNA Purification Kit. In this method DNA is absorbed on to a silica membrane at pH 5 followed by buffered alcohol wash and elution at pH 8.5. Product was visualized on 6% polyacrylamide gel by ethidium bromide staining and ultraviolet illumination. The final yield was approximately 2.5 µg of each at concentrations of 50 ng/µl. Sequence of each cassette amplicon was verified by cycle sequencing with BigDye Terminators, using forward and reverse PCR primers on an ABI Prism 310 as described above.

Restriction Enzyme Linkage of CFTR Exon 10 and 11 Cassettes.

Figure 3:
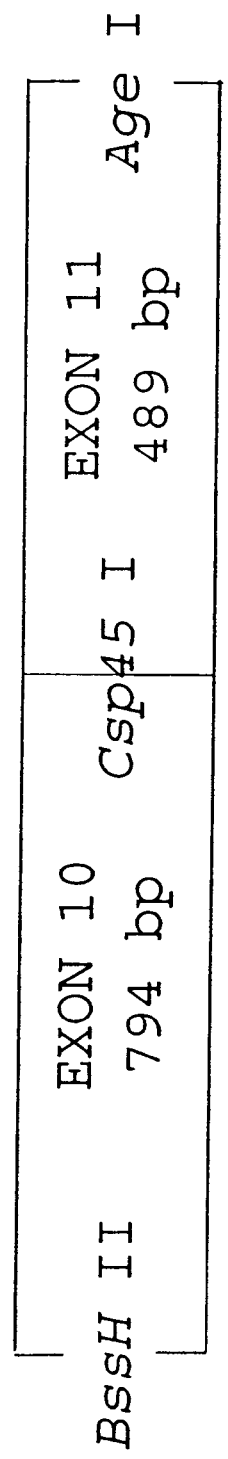
FIG. 3 is a diagram of the restriction enzyme scheme used for linkage of the exon 10 and 11 cassettes.

The amplicons were ligated by their common restriction site, Csp45 I TT*CGAA (FIG. 3). The "rapid" ligation/cloning was performed as follows. The DNA concentration for exon 10 was 50 ng/µl and 98 ng/µl for exon 11. The digest reaction mixture comprised the following: 2 µl dH2O, 2 µl 10× Buffer B (60 mM Tris-HCl, pH 7.5, 60 mM MgCl$_2$, 500 mM NaCl), 2 µl 10× BSA, 9 µl exon 10 cassette (450 ng), 4 µl exon 11 cassette (450 ng), and 1 µl Csp45 I (10 units/µl). The mixture was incubated at 37° C. overnight. Csp45 I was deactivated at 65° C. for 15 minutes. Ligation of the fragments was performed by adding directly to the digest 2 µl of 10× Ligase buffer (300 mM Tris-HCl, pH 7.8, 100 mM MgCl$_2$, 100 mM ATP) and 6U of T4 DNA Ligase. The mixture was mixed and incubated at 25° C. for 4 hours.

Insertion of Linked CFTR Exon 10–11 Cassette into Expression Vector.

The linked CFTR exon 10–11 cassette was ligated using its A overhangs into pGEM-T plasmid by addition of the following to the ligation reaction described above: 10 µl 2× pGEM-T Buffer, 2.5 µl pGEM-T Vector (50 ng/µl), and 2 µl T4 Ligase (4.0 Weiss units/µl). The mixture was incubated at 4° C. overnight. 10 µl of ligation reaction product was precipitated by mixing with 1 µl glycogen, 5 µl of 7.5 M ammonium acetate, and 30 µl of 100% ethanol and incubation at −70° C. for 10 minutes. The precipitate was separated by centrifugation at 12,000×g and was washed with 50 µl of 70% ethanol. After drying the sample was dissolved in 10 µl of nuclease free DI water.

Transformation of Bacterial Cells with Linked CFTR Exon 10–11 Clones.

Electroporation was performed with the Bio-rad GenePulser™ (Bio-Rad Laboratories, Richmond, Calif.) followed by 1 hour incubation in S.O.C. medium and plating on LB/ampicillin plates.

The transformation protocol was performed as follows. Cuvettes were chilled on ice. Electrocompetent cells, Top10F' (Invitrogen, Carlsbad, Calif.) were thawed on ice. One µl of plasmid DNA was added to 40 µl cell suspension, the suspension was mixed gently, and then incubated on ice for 1–2 minutes. The cell/plasmid DNA suspension was transferred to a cold cuvette and electroporation was conducted at 1.6 kV, 25 µf, 200 ohms, with a pulse of 4–5 mseconds. 960 µl of SOC medium, (2% tryptone, 0.5% yeast extract, 10 mM NaCl, 2.5 mM KCl, 10 mM MgCl$_2$, 10 mM MgSO4, 20 mM glucose) was added immediately to cuvette. The cells (in SOC) were transferred immediately to a test tube and incubated 1 hour at 37° C. with agitation. Electroporated cells were streaked on plates with selective L/B ampicillin media and incubated overnight at 37° C.

Selection and Isolation of Linked CFTR 10–11 Clone.

Colonies were screened for the presence of the appropriately sized insert by picking a colony directly into a PCR reaction. M13 primers were used in the PCR reaction and cycling conditions were 95° C. for 1 minute, 30 cycles of 95° C. for 20 seconds, 52° C. for 60 seconds, 72° C. for 60 seconds, a hold of 72° C. for 10 minutes, and final hold at 4° C. PCR products of the colony screen were run on 6% polyacrylamide gel with ethidium bromide staining and ultraviolet-light visualization. The expected size of the cassette ligation product was 1,274 basepairs (bp). Using the M13 primers added 204 bases to the PCR product for a total expected product of 1,478 bp size from colony screen.

As happens occasionally, especially when the insert is an even number of bases, the only positive clones were light blue colonies. These were picked and cultured in LB/amp media and purified by the Wizard Plus miniprep kit as described previously elsewhere herein. Recovered plasmid was sequenced in both directions using pUC M13 primers using the sequencing conditions and system described above for cycle sequencing with BigDye Terminators. Sequence analysis was performed using an ABI Prism 310. Both exon 11 and exon 10 sequences was found to be wild type. A 3 ml culture of a positive clone was grown overnight and then mixed with 2 ml sterile glycerol and frozen at −70° C. This clone was designated the CFTR 10–11 clone.

EXAMPLE 3

Mutagenesis of Linked CFTR Exon 10–11 Clone by Site Directed Mutagenesis of the Exon 10–11 Ligation Product The experiments presented in this example may be summarized as follows.

The data disclosed herein demonstrate construction of restriction site-linked CFTR exons 10–11 clones containing mutations introduced by mutagenesis of a CFTR exon 10–11 ligation product.

The Materials and Methods used in the experiments presented in this example are now described.

Site-Directed Mutagenesis

One approach to production of clones containing mutant sequences is the direct mutagenesis of the ligation product. Site-directed mutagenesis is considered significantly more accurate than PCR-based mutagenesis. The QuikChange™ Site-Directed Mutagenesis Kit (Stratagene, La Jolla, Calif.) was used to introduce the deltaF508 and deltaI507 mutations into a construct. Primers were designed strictly according to manufacturer guidelines and have the following properties: both mutagenic primers contain the desired mutation and anneal to the same sequence on opposite sides of the plasmid, primers should be between 25 and 45 bases in length having a melting temperature of greater than or about 78° C., the desired mutation should be in the middle of the primer with about 10–15 bases of correct sequence on both sides, primers have a minimum GC content of about 40% and terminate with one or more C or G bases, and primers are not 5′ phosphorylated and are preferably purified using fast polynucleotide liquid chromatography or polyacrylamide gel electrophoresis.

The primer oligonucleotides were ordered from Integrated DNA Technologies (IDT) and were PAGE-purified. The mutagenesis primer pairs were as follows: Primer #1: CFMUTAGDEL507 (Tm=81° C.): 5′-GCC TGG CAC CAT TAA AGA AAA TAT CTT TGG TGT CTA TG-3′ (SEQ ID NO:5); primer #2 COMPCFMUTAGDEL507: 5′-CAT AGG AAA CAC CAA AGA TAT TTT CTT TAA TGG TGC CAG GC-3′ (SEQ ID NO:6); primer #3 CFMUTAGDEL508 (Tm=83° C.): 5′-GCC TGG CAC CAT TAA AGA AAA TAT CAT CGG TGT TTC CTA TGA TG-3′ (SEQ ID NO:7); primer #4 COMP CFMUTAGDEL508: 5′-CAT CAT AGG AAA CAC CGA TGA TAT TTT CTT TAA TGG TGC CAG GC-3′ (SEQ ID NO:8).

The deltaF508 mutation was introduced according to the following protocol. Briefly, primers were reconstituted to a 10× concentration of 100 nmole/ml. Three concentrations of ligation template were run in the deltaF508 mutagenesis experiment as follows: 0.5 μl (14 ng), 1 μl (28 ng), or 2 μl (55 ng) ligation template, 5 μl of 10× reaction buffer (200 mM Tris-HCl, pH 8.8, 100 mM KCl, 100 mM $(NH_4)_2SO_4$, 20 mM Mg $SO_4$, 1 mg/ml bovine serum albumin (BSA)), 1.25 μl Primer #3, 1.25 μl Primer #4, 1 μl PfuTurbo DNA polymerase (2.5 U/L), dH2O to final volume of 50 μl. The reactions were cycled in a PE 9700 thermal cycler (Perkin-Elmer, Foster City, Calif.) as follows: 95° C. for 30 seconds, 18 cycles of 95° C. for 30 seconds, 55° C. for 1 minute, 68° C. for 9 minutes, and a final hold at 4° C.

The reactions were digested with Dpn I by adding 1 μl Dpn I (10 units/μl) to the reaction mixture and incubating at 37° C. for 1.25 hours. One μl of each digest was added directly to 50 μl of Stratagene XL1-Blue supercompetent cells, mixed for 30 minutes on ice, and transformed by heat pulse into the Blue cells. Briefly, the protocol for heat pulse was: 45 seconds at 42° C. in Falcon 2059 polypropylene tubes. 0.5 ml of S.O.C. medium, preheated to 42° C., was added and the reaction was incubated at 37° C. for 1 hour with shaking. The transformation product was plated on LB/ampicillin plates and incubated at 37° C. for 24 hours.

For incorporation of the deltaI507 mutation into the exon 10 fragment, the same mutagenesis protocol was followed using Primers #1 and #2 (SEQ ID NOS:5 and 6, respectively). Two reactions were set up, one with 15 ng of template and one with 41 ng. Cycling parameters were the same as for introduction of the deltaF508 mutant sequence as described above, as were procedures for digestion, transformation, and selection.

The Results of the experiments presented in this Example are now described.

With regard to the deltaF508 mutation, the data disclosed herein demonstrate that there were greater than 250 colonies on all plates. More than 90% of the control colonies were positive for transformation (dark blue) and more than 90% of the ligation colonies were positive (pale blue/white). Six colonies were sequenced. All clones contained the deltaF508 mutation. No other base changes were seen in the first 600 bases of exon 10. One clone carrying the deltaF508 mutation was cultured overnight and then mixed with sterile glycerol and frozen at −70° C. This clone was termed the CFTR10–11d508 clone. The entire insert of this clone was sequenced and the entire sequence was found to be unchanged with respect to wild type except for the deletion of the 508 codon.

The data disclosed herein demonstrate that in the case of the deltaI507 mutation, more than 90% of the colonies appeared positive on both plates. Four colonies were cultured, purified, and sequenced. All four clones carried the deltaI507 mutation. Approximately 600 bases of exon 10 were sequenced and were demonstrated to be unchanged compared with the starting sequence template. One clone carrying the deltaI507 mutation was cultured and then mixed with sterile glycerol and frozen at −70° C. This clone was designated the CFTR10–11d507 clone. The entire insert of this clone was sequenced and all sequence was found to be unchanged compared to the initial sequence.

EXAMPLE 4

Mutagenesis of Linked CFTR Exon 10–11 Clone Removal, Mutagenesis and Replacement of the Cloned Cassette The experiments presented in this example may be summarized as follows.

The data disclosed herein describe the construction of restriction site-linked CFTR exons 10–11 clones containing mutations introduced by clone removal, mutagenesis, and replacement of the cloned cassette.

The Materials and Methods used in the experiments presented in this example are now described.

Removal and Isolation of CFTR Cassettes.

Figure 4:
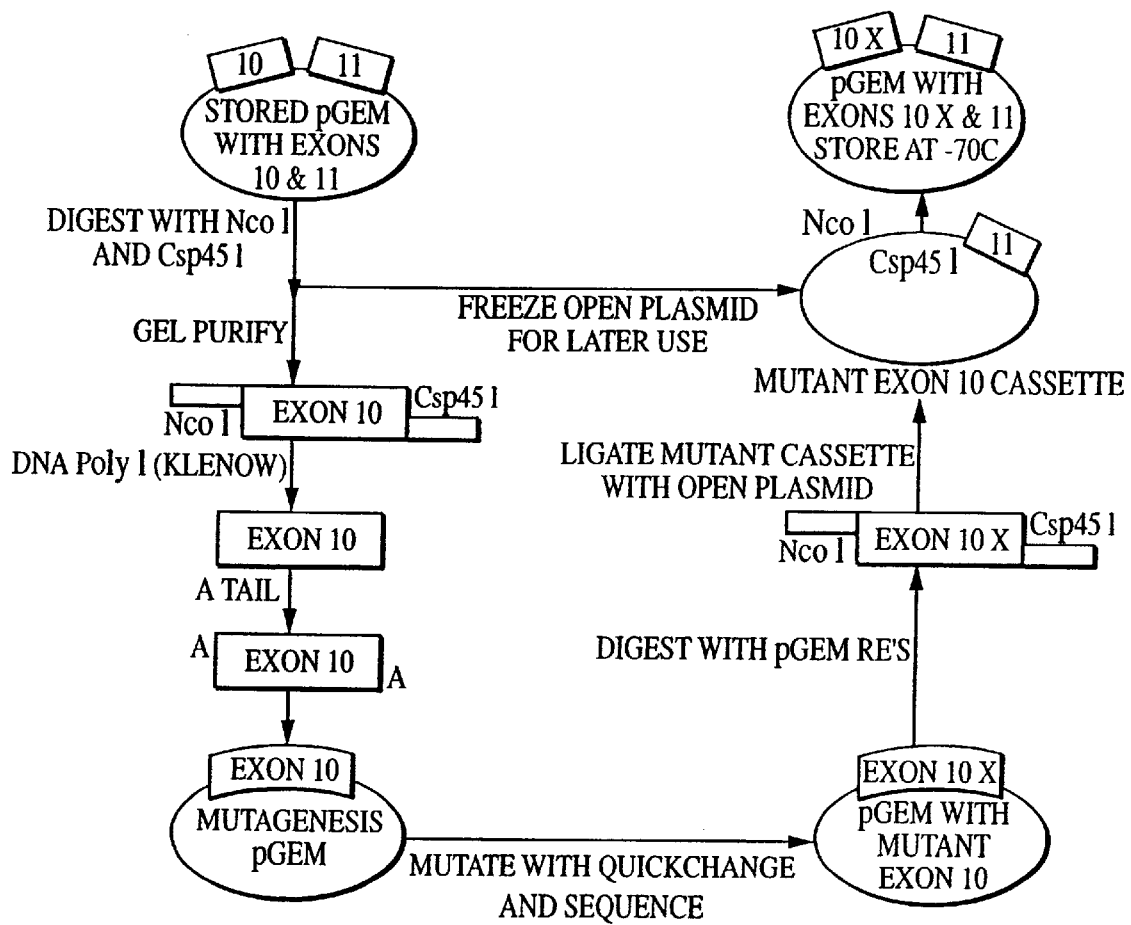
FIG. 4 is a diagram depicting the scheme for removal, mutation, and replacement of the nucleic acid cassette.

The Exon 10 insert was removed from the ligated wild-type clone produced in Example 2, supra. Nco I was used to digest the 5' end of the insert from the vector and Csp45 I digested the 3' end of the insert free from the exon 11 cassette. The scheme by which the insert was removed from the cassette is depicted in FIG. 4. Nco I was selected because the restriction site was present in the pGEM-T vector 5' of the exon cassette and was close to the cloning site. A simultaneous digestion was set up using Buffer B and a 40 µl reaction ensured sufficient product was obtained from the gel extraction.

The digest reaction was performed as follows: 4 µl Buffer B (60 mM Tris-HCl, pH 7.5, 60 mM $MgCl_2$, 500 mM NaCl); 4 µl 10× BSA; 4 µl exon 10/11 ligation fragment in vector; 2 µl Csp45 I (10 U/µl); and 2.1 µl Nco I (10 U/µl). The reaction was incubated at 37° C. for 4 hours and heat inactivated for 15 minutes at 65° C.

The digest was electrophoresed on a 1% agarose gel. The digest products were extracted using the QIAquick Gel Extraction Kit according to manufacturer protocol. The yield was 1.4 µg of pGEM and 2 µg of exon 10. Purified, linearized pGEM was frozen for future use.

Ligation of "Removed" Exon 10 into Vector

The purified exon 10 fragment was treated with Klenow to fill in the restriction enzyme cuts and then ligated into fresh pGEM as follows. A Klenow reaction mixture was prepared comprising: 3 µl 10× Klenow Buffer (200 mM Tris-HCl, pH 7.6, 100 mM $MgCl_2$, 15 mM β-mercaptoethanol, 25 mM dithiothreitol), 0.6 µl 10× BSA, 2.4 µl dNTP mix (0.5 mM each), 25 µl exon 10 cassette digest (1 µg), and 0.6 µl Klenow Fragment (1 U/µl) (Promega Corp., Madison, Wis.).

The Klenow reaction was incubated at room temperature for 12 minutes and then inactivated at 75° C. for 10 minutes. The reaction product was purified by standard alcohol precipitation, reconstituted in 25 µl of DI water and poly A-tailed according to the following protocol as recommended by the manufacturer (Promega Corp.). That is, a poly-A tail reaction mixture was prepared comprising: 1 µl 10× Taq buffer (500 mM KCl, 100 mM Tris-HCl, pH 9.0, 1% Triton® X-100), 1 µl $MgCl_2$ (to a final concentration of 25 mM), 2 µl dATP (final concentration of 0.2 mM), 3 µl purified fragment, 1 µl Taq DNA Polymerase (5 units), and 2 µl dH2O. The poly-A tailing reaction was incubated at 70° C. for 30 minutes.

The Klenow-filled and polyadenylated insert was then ligated into pGEM-T as follows. Briefly, a ligation mixture was prepared comprising: 5 µl 2× Buffer, 1 µl pGEM-T (50 ng/µl), 3 µl poly A-tailed product obtained directly from the reaction described above, and 1 µl T4 Ligase (4 Weiss units/µl).

The ligation reaction was incubated overnight at 4° C. The ligation reaction was purified for electroporation using ammonium acetate buffered alcohol precipitation. Electroporation was performed with the BioRad GenePulserTM, followed by 1 hour incubation in S.O.C. medium and plating on Luria Broth (LB)/ampicillin plates according to the methods described previously elsewhere herein. White colonies were selected and grown in culture, and small scale preparations (minipreps) were performed on these cultures and using Promega's Wizard Plus Miniprep Kit according to manufacturer's instructions. Isolated plasmid was sequenced in both directions using pUC M13 primers to confirm the integrity and directionality of the "removed" exon 10 insert.

Site-Directed Mutagenesis of the "Removed" Exon 10 Cassette Clone

Three exon 10 cassette mutagenesis reactions were run using three different amounts of ligation product disclosed previously, i.e., 75 ng (ligation 1), 375 ng (ligation 2), and 1.5 µg of ligation product (ligation 3). Thermalcycling parameters were as described previously elsewhere herein.

The Results of the experiments presented in this Example are now described.

Plating of bacteria transformed with the "excised" exon 10 ligated into fresh pGEM resulted in growth of more than 500 transformant colonies. Approximately 10% of the colonies were white. Fourteen white colonies and seven blue (i.e., negative) colonies were cultured and purified. Minipreps from three blue and seven white colonies were sequenced in both directions using pUC M13 primers. The three blue colonies contained only vector. Of the seven white colonies, one colony contained only vector, 4 colonies contained the insert in a 3' to 5' orientation, and two colonies contained the insert in a 5' to 3' orientation. All inserts had restored Csp45 I sites, which demonstrates that the cassette scheme worked as designed.

Following mutagenesis of the cloned "excised" exon 10 cassette, mutagenesis products were digested, transformed in bacteria, and plated. Greater than 90% of the colonies were positive (white). Approximately ten colonies grew on plate for ligation 1, supra, about 20 per plate were obtained using ligation 2, supra, and about 100 per plate were obtained using ligation 3, supra. Ten colonies, at least two from each plate, were cultured and purified using the QIAprep Spin Miniprep Kit (Qiagen, Chatsworth, Calif.) according to manufacturer's protocol as described previously elsewhere herein. Five of the minipreps were sequenced in both directions with pUCM13 primers, and all five carried the deltaF508 mutation.

The mutated exon 10 cassette is excised from the pGEM-T vector by digestion with Csp45 I and Nco I and poly A-tailed using the protocol described above. The mutated exon 10 cassette is then ligated into the saved exon 11 containing pGEM fragment using a pGEM ligation reaction as described previously elsewhere herein. The product is plated, positive colonies are cultured, and plasmid is separated using a miniprep protocol as described previously elsewhere herein. The plasmid is purified and the insert is sequenced using the exon cassette 10 and 11 and pUCM13 primers as described previously elsewhere herein. The product is sequence demonstrated complete Exon 10 and Exon 11 cassettes and demonstrated that the Exon 10 cassette had the deltaF508 mutation. A positive clone is cultured overnight and then mixed with sterile glycerol and aliquots are frozen at −70° C.

The procedure disclosed herein can be modified such that removing, mutating and replacing cassettes is direct mutagenesis of the ligation product containing the removed exon without first growing it up in a clone. This variation saves at least 2 days of culture and colony screening, which are important considerations in constructing a comprehensive CF control set with multiple exon cassettes comprising multiple mutations.

The data disclosed herein demonstrate that such rapid mutagenesis is feasible as demonstrated by setting up a QuikChange mutagenesis reaction as previously described for deltaF508 mutation. That is, mutagenesis was performed directly on the excised exon 10 cassette that had been ligated into pGEM-T, but which had not yet transformed into *E. coli*. This direct mutation of ligated product protocol yielded a lower number of colonies on culture, but mutagenesis efficiency remained greater than 90% demonstrating the usefulness of this approach.

EXAMPLE 5

Preparation and Testing of Reference DNA Cassettes.

The experiments presented in this example may be summarized as follows.

The data disclosed herein demonstrate preparation of reference DNA cassettes and their testing in two commercial CF test systems demonstrating the usefulness of the present invention in nucleic acid assays.

The Materials and Methods used in the experiments presented in this example are now described.

Preparation of Reference DNA Cassette Solution

Reference samples of DNA at a known concentration in solution were produced by removing aliquots of frozen, cloned, CFTR10–11, CFTR10–11d508 and CFTR10–11d507 constructs. The clones were grown overnight in 3 ml of LB/ampicillin broth. The plasmids were separated and purified using the Wizard Plus protocol as set forth previously elsewhere herein. The plasmid concentration was quantified by ultraviolet spectrophotometry as described in Sambrook et al., supra, and the number of plasmids per microliter was calculated.

Roche Linear Array CF-31 Assay

The Roche Linear Array CF-31 assay (Roche Diagnostics Corporation, Indianapolis, Ind.), a well-known art-recognized assay for identifying nucleic acid samples comprising mutations in the CFTR gene, was performed at the referee clinical laboratory of the University of North Carolina (UNC). This test directly evaluates the CFTR gene for the presence of genetic mutations G480C, DI507, DF508, and polymorphisms F508C, I507V, I506V in exon 10, and mutations 11 G542X, G551D, R553X, A559T, R560T in exon 11 and mutation 1717-1 G to A in intron 10.

To evaluate the detection limit of the test system, a clone of exon 10/11 ligation fragment having wild-type sequence was cultured and purified using Wizard Plus Miniprep Kit per manufacturer's instructions. The DNA concentration of the miniprep was 585 ng/$\mu$l. Since 1 $\mu$g of plasmid-CF ligation fragment contains $2.14 \times 10^{11}$ DNA copies, the miniprep has $1.24 \times 10^{11}$ copies/$\mu$l. After an initial dilution of $1:2 \times 10^4$, the plasmid was serially diluted in TE buffer (10 mM Tris, 0.1 nM EDTA, pH 8.0) as follows: tube 1=62× $10^4$copies/$\mu$l; tube 2=62×$10^3$ copies/$\mu$l; tube 3=62×$10^2$ copies/$\mu$l; tube 4=620 copies/$\mu$l; and tube 5=62 copies/$\mu$l.

Two microliters each of tubes 3, 4, 5 were amplified in duplicate in a standard 50 $\mu$l PCR reaction using Amplitaq Gold for either 32 cycles, as in the Roche Linear Array, or for 35 cycles.

In the Linear Array test, samples containing the exons 10 and 11 and intronic borders were PCR amplified using a combination of 2 biotin labeled primers. 25 $\mu$l of sample were incubated 30 seconds at 93° C. with 10 $\mu$l 10× PCR buffer (500 mM KCl, 100 mM Tris, pH 8.0), 10 $\mu$l CF primer mix (1.2 mM), 1.5 $\mu$l 100 mM dNTP (with 200 mM dUTP) mix (3 mM dATP, dCTP, dGTP and 6 mM dUTP), 3 $\mu$l Uracil n-glycosylase(1U/$\mu$l), 3 $\mu$l Taq DNA polymerase (5U/$\mu$l), 22.5 $\mu$l nuclease free H$_2$O. 25 $\mu$l of 32 mM MgCl$_2$ were added and the mixture was subjected to the following thermal cycling: hold for 10 minutes at 42° C., hold for 1 minute at 93° C., cycle (32 cycles) 30 seconds at 93° C., 30 seconds at 60° C., 1 minute at 72° C., followed by hold for 10 minutes at 72° C. followed by final hold of up to 2 hours at 15° C.

Post amplification, 80 microliters of each PCR reaction were added to a well in a sterile microplate and 80 microliters of denaturation solution were added to each sample and the samples was mixed gently. Sufficient pre-warmed 37° C. Hybridization/wash buffer (0.6 M NaCl, 33.3 mM NaH$_2$ PO$_4$, 3.3 mM Na$_2$EDTA, pH 7.4, in 0.5% SDS) was added to cover the Linear Assay profile (LAp) (approximately 5 ml/panel). Seventy microliters of denatured PCR product were added to each LAp, and then incubated at 50° C. for 20 minutes with gentle shaking.

After incubation, the buffer was removed by aspiration and hybridization/wash buffer was added to each LAp, followed by gentle mixing (5–6 times). The Hybridization/wash buffer was removed by aspiration and fresh conjugate solution (5 ml Hybridization/wash buffer and 20 microliters of streptavidin-POD) was added to the LAp, followed by gentle agitation for 20 minutes at 50° C. Conjugate solution was removed by aspiration and fresh Hybridization/wash buffer was added to the Lap, followed by gentle agitation for 10 minutes at 50° C. Hybridization/wash buffer was removed by aspiration and Citrate buffer (0.1 M sodium citrate, pH 5.0) was added, followed by gentle agitation for 10 minutes at room temperature.

Color development was performed as follows. The citrate buffer was removed by aspiration and fresh substrate solution (5 ml of citrate buffer, 5 microliters of 3% hydrogen peroxide and 250 microliters of TMB (tetramethylbenzidine) solution (2 mg TMB/ml of 100% ethanol)) was added to the LAp. Each strip was kept covered to prevent excessive exposure to light, and gently agitated for 10–20 minutes at room temperature. Substrate solution was removed by aspiration and deionized water was added to the LAp. Each strip was gently agitated for 10–20 seconds at room temperature. The water was removed by aspiration and replaced with fresh deionized water, followed by gentle agitation for 5 minutes at room temperature. LAps were removed, sealed in a hybridization bag, and read within 30 minutes using the Roche CF-31 Linear Array Reference Guide.

Applied Biosystems PCR/OLA/SCS Test for CFTR Mutations.

The Applied Biosystems PCR (Polymerase Chain Reaction)/OLA (Oligonucleotide Ligation Assay)/SCS (Sequence-Coded Separation) CFTR mutation assay is a capillary electrophoresis technique. The oligonucleotide ligation assay involves PCR amplification of the gene segment of interest, hybridization with two probes and ligation of the probes only if probe sequence matches the amplified sequence. The ligated probe product is detected by electrophoresis and fluorimetric detection.

Figure 6B:
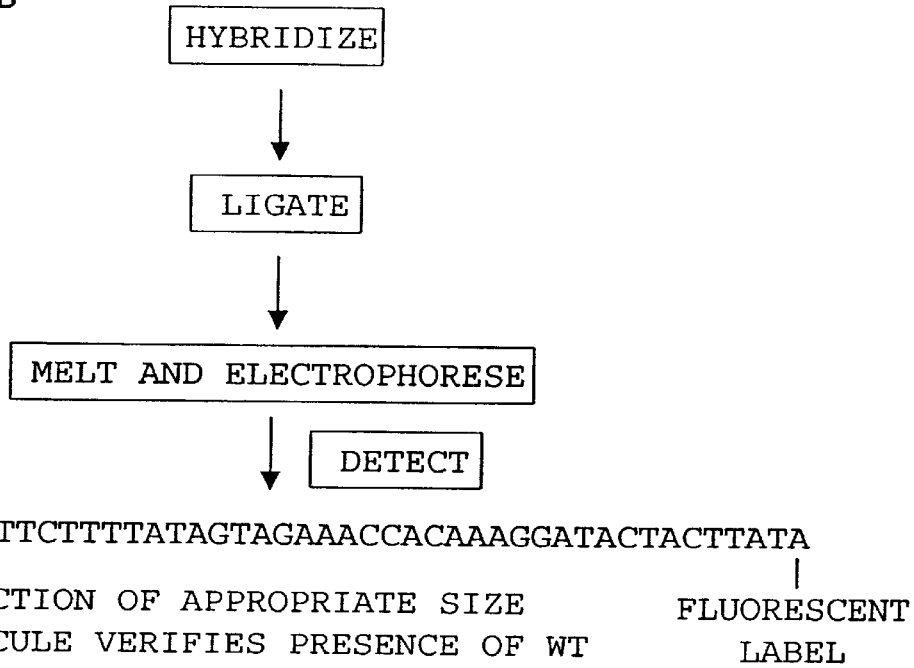
Figure 6C:
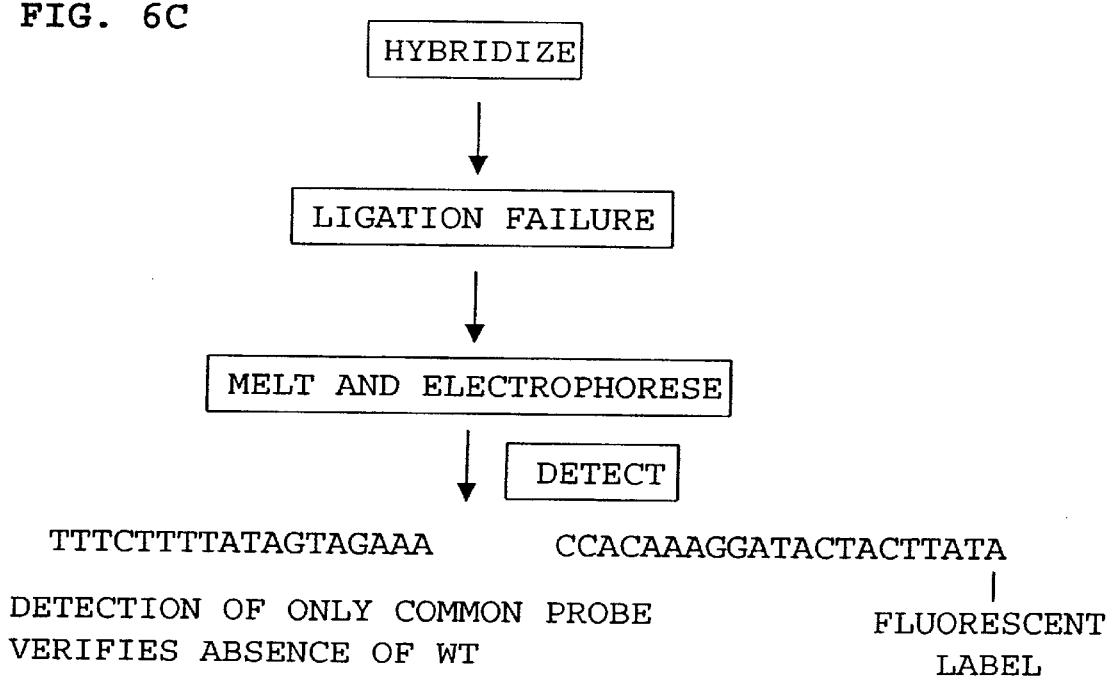

For any given mutation to be tested there is a fluorescent common probe, a wild type (wt) probe, and a mutant probe (mt). The wt and mt probes contain the complementary sequence for the region 5' to the mutant site. The 3' ends of these probes contain the base complementary to wt or mt at the site. The common probe contains sequence complementary to the region 3' to the mutant site. The common probe is designed to bind to the amplified sequence. If either wt or mt probe matches the amplified sequence at the 3' end then they bind in alignment to each other and are ligated by DNA ligase. If the 3' end of either the mt or wt probe does not match the mutant site then that probe will not be ligated. The mt and wt probes are of different length so the ligated products from each of these are separated by electrophoresis. They are detected by detection of the fluorescent molecule attached to the common probe. Homozygous sample will yield a single fluorescent band on electrophoresis of the molecular size of common probe linked to either wt or mt probe. Heterozygous sample will yield two fluorescent bands on electrophoresis of the molecular size of common probe linked to wt and common probe linked to mt probe. FIG. 6 illustrates the principle of the Applied Biosystems PCR/OLA/SCS. Although the entire lengths of the probes and sample sequences are not provided herein, representative segments are shown as examples of the principle and the complete sequences are available.

The Applied Biosystems (ABI) Cystic Fibrosis System is a one-day assay that uses a single reaction tube and a single lane (or capillary) of an electrophoresis run, which assay is well-known in the art. Samples CFTR10–11, CFTR10–11d508 and CFTR10–11d507 were each tested in this assay. All samples tested were adjusted to a concentration of approximately 60,000 DNA copies per microliter. A single-tube, 15-plex PCR of the Cystic Fibrosis Transmembrane Conductance Regulator (CFTR) gene was followed by a 60-plex OLA in the same tube. Since these samples contained only exon 10 and exon 11 cassettes, only those regions amplified in the 15 plex PCR.

Electrophoresis separated the products from the three-color, multiplex OLA in a single lane of a four-color fluorescent DNA analyzer (ABI 373 and ABI 377 DNA Sequencers or the ABI 310 Genetic Analyzer). The ABI Genotyper Software analyzed the data and the CF Genotyper Template Software created a mutation summary, a CF Genotype for all loci tested.

The Results of the experiments presented in this Example are now described.

Reference DNA cassette samples were tested by sequencing directly from the plasmid miniprep. They were also tested in two commercial CF nucleic acid assay systems, an earlier version of the Roche Linear Array® CF-31, and Applied Biosystems PCR/OLA®, both designed for clinical testing.

Sequencing was performed using the primers from original cassette amplifications and sequencing chemistry as described previously elsewhere herein. The sequencing result detected the wt sequence for CFTR10–11 and detected codon 508 missing in the CFTR10–11d508 clone and codon 507 missing in the CFTR10–11d507 clone. The rest of the codons from these clones were present in wt sequence. The results of the testing are depicted in Table 1.

TABLE 1

| Sample | B CFTR10-11d508 | | | C CFTR10-11d507 | | | Level 1 CFTR10-11 | | Level 2 CFTR10-11 | | Level 3 CFTR10-11 | | |
|---|---|---|---|---|---|---|---|---|---|---|---|---|---|
| Laboratory | UNC | AB | MMQCI | UNC | AB | MMQCI | UNC | MMQCI | UNC | MMQCI | UNC | AB | MMQCI |
| Exon | | | | | | | | | | | | | |
| 10 | Y | Y | Y | Y | Y | Y | nd | Y | Y | Y | Y | Y | Y |
| 11 | Y | Y | Y | Y | Y | Y | nd | Y | Y | Y | Y | Y | Y |
| Mutation Site | | | | | | | | | | | | | |
| G480 | wt | wt | wt | wt | Wt | wt | nd | wt | wt | wt | wt | wt | wt |
| Q493 | wt | wt | wt | wt | Wt | wt | nd | wt | wt | wt | wt | wt | wt |
| ΔI507 | nd | wt | wt | MT | MT | MT | nd | wt | wt | wt | wt | wt | wt |
| ΔF508 | MT | MT | MT | nd | Wt | wt | nd | wt | wt | wt | wt | wt | wt |
| V520 | wt | wt | wt | wt | Wt | wt | nd | wt | wt | wt | wt | wt | wt |
| 1717-1 | wt | wt | wt | wt | Wt | wt | nd | wt | wt | wt | wt | wt | wt |
| G542 | wt | wt | wt | wt | Wt | wt | nd | wt | wt | wt | wt | wt | wt |
| S549 | wt | wt | wt | wt | Wt | wt | nd | wt | wt | wt | wt | wt | wt |
| G551 | wt | wt | wt | wt | Wt | wt | nd | wt | wt | wt | wt | wt | wt |
| R553 | wt | wt | wt | wt | Wt | wt | nd | wt | wt | wt | wt | wt | wt |
| A559 | NA | NA | NA | NA | NA | NA | nd | wt | NA | wt | NA | wt | wt |
| R560 | wt | wt | wt | wt | Wt | wt | nd | wt | wt | wt | wt | wt | wt |
| Polymorphism | | | | | | | | | | | | | |
| I506V | wt | wt | wt | wt | Wt | wt | wt | wt | wt | wt | wt | wt | wt |
| I507V | wt | wt | wt | wt | Wt | wt | wt | wt | wt | wt | wt | wt | wt |
| F508C | wt | wt | wt | wt | Wt | wt | wt | wt | wt | wt | wt | wt | wt |
|  | Strong Signal | Strong Signal | Expected Sequence | Strong Signal | Strong Signal | Expected Sequence | No Signal | Expected Sequence | Moderate Signal | Expected Sequence | Strong Signal | Strong Signal | Expected Sequence |
| Concentration Copies per μl | $3 \times 10^4$ | | | $6 \times 10^4$ | | | $6 \times 10^2$ | | $6 \times 10^3$ | | $6 \times 10^4$ | | |

UNC refers to testing done at the referee laboratory at the University of North Carolina, Raleigh, NC;
AB refers to testing done at Applied Biosystems in Foster City, CA;
MMQCI refers to data on the control sample sythesized at Maine Molecular Quantity Controls, Inc.;
wt = wild type,
MT = mutation,
nd = not detected,
NA = not measured.

Figure 5:
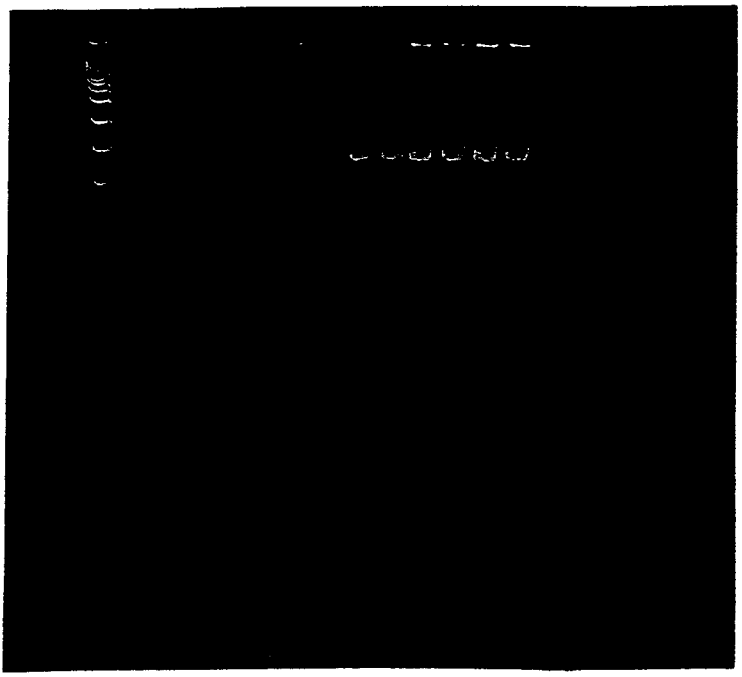
FIG. 5 is an image of a polyacrylamide gel stained with ethidium bromide.

To evaluate the detection limit of the Roche Linear test system, including determining what dilution would most likely give a strong signal in the Roche and AB systems without contaminating other samples, PCR amplification was performed on varying concentrations of wild-type plasmid, as described previously elsewhere herein. Thirty-five cycles produced a significant amount of product in all tubes as visualized on 6% polyacrylamide ethidium bromide-stained gels (FIG. 5). Amplification was repeated, cycling for only 32 cycles, as in the Roche Linear Array. The amplification product gave a faint signal in Tube 5 ($62 \times 10^0$ copies/μl), stronger signal in Tube 4 ($62 \times 10^1$ copies/μl), and strong signal in Tube 3 ($62 \times 10^2$ copies/μl).

Samples of CFTR10–11 were tested at various concentrations, i.e., 620, 6,200, and 62,000 copies per microliter, in the Roche Linear Array system. Samples at the 620 copies per microliter level (Level 1) did not give sufficient signal for analysis. Samples at the 6,200 (Level 2) and 62,000 copies per microliter level (Level 3) both gave results interpretable by the test (See Table I, UNC laboratory, Level 1, Level 2, Level 3).

Product samples were also tested for CFTR mutations at Applied Biosystems, Foster City, Calif. The testing demonstrated wild type sequences for the CFTR Exon 10 and Exon 11 mutations evaluated for Sample CFTR10–11 (See Table I, AB laboratory, Level 3). Sample CFTR10–11d508 tested positive for the exon 10 deltaF508 mutation and the sample CFTR10–11d507 tested positive for the deltaI507 mutation (See Table I, AB laboratory, columns B and C, respectively.) These data demonstrate the use of the methods and cassettes of the invention to produce synthetic products containing specifically designed DNA segments and mutations and that are useful reference materials in a genetic test.

The production of the sample yielding a CFTR deltaI507 homozygous result in the DNA tests (Sample C, Table 1) demonstrates the utility and value of this approach for making reference materials for genetic testing. The deltaI507 mutation is present in only 0.2% of the population. Homozygotes for this mutation are therefore quite rare and laboratories will not readily have archived patient specimens available for validation of testing capability to detect the homozygous deltaI507 patient. Thus, use of the instant invention provides needed reference nucleic acids that cannot be readily obtained and which provide stable, reproducible and simple reference standards for use in a wide variety of nucleic acid assays.

The exceptionally numerous disease-causative mutations found in the cystic fibrosis transmembrane conductance (CFTR) gene, as well as the large size of the gene (230 kilobases), render this gene particularly difficult to assess the presence or absence of mutations associated with CF using prior art techniques. Indeed, since the identification of the CFTR gene as the cause of CF (Rommens et al., 1989, Science 245:1066–1073; Riordan et al., 1989, Science 245:1066–1073; Kerem et al., 1989, Science 245:1073–1080), more than 800 mutations and DNA sequence variations have been detected (Castaldo et al., 1999, Clin. Chem. 45:957–962). Over 350 of these are presumed to be pathologic mutations and it is expected that many more will be identified (Welsh et al., 1995, In: The metabolic and molecular basis of inherited disease, pp. 3799–3876, Scriver et al., eds., 7$^{th}$ Ed., McGraw-Hill, New York).

The data disclosed herein demonstrate a carefully designed, flexible system of CFTR gene fragments, carrying both mutated and wild-type sequence, ligated so that, as new mutations are discovered, modifications and additions to the construct can be easily effected. Further, constructs can be used to produce stable nucleic acid reference standard, for example, the DNA construct can be transformed into *Escherichia coli,* which will be killed and fixed for final control production as described in U.S. Pat. Nos. 5,994,078, and 6,013,434. A portion of the *E. coil* carrying the construct can be stored in viable form to provide a renewable source of construct for control production.

A final construct comprises all 27 CFTR exons and their intronic borders because this is where most of the disease-causative mutations are found. It is a significant improvement over prior art method that the present invention easily allows additional fragments to be added. This is because, although few laboratories currently test for mutations far into the non-coding regions, increasing evidence of phenotype correlation with newly discovered mutations indicates the possibility that significant mutations may also occur in these regions (Friedman et 1., 1999, Clin. Chem. 45:929–931). Consequently, the ability to add fragments to the control construct, and to modify the construct to include newly-discovered mutations/variations/polymorphisms in the future is an important advantage over prior art constructs.

Further, the nucleic acid controls of the invention have many advantages over patient-derived materials. The flexible design of the construct allows representation of all alleles appropriate for a particular test menu, including the rarer mutations that occur in certain populations. Further, the control of the invention can be easily engineered to comprise one or two desired mutations or, alternatively, many mutations can be included if this is advantageous in the test system.

In contrast, DNA extracted from patients can represent only one genotype and it is difficult for small laboratories to obtain the rarer genotypes from their limited patient population. In fact, maintaining a supply of patient material of only the 24 most frequent CF mutations identified by the Cystic Fibrosis Foundation Consensus Panel (Rosenstein et al., 1998, J. Pediatrics 132:589–595) can be difficult because, except for the deltaF508 mutation, no other single mutation accounts for more than five percent of CF chromosomes in most populations (Eggerding et al., 1995, Human Mutation 5:739–745). Furthermore, the uncertain stability of frozen DNA necessitates periodic handling of potentially infectious materials in order to replenish the control supply, while the controls disclosed herein provides a continual, stable, abundant, non-infectious source of material.

Although patient-derived control material may be sufficient for those laboratories testing for a limited number of common mutations, issues of patient confidentiality may soon make that material difficult to obtain. The Clinical Laboratory Improvement Advisory Committee (CLIAC) has recommended that reuse of anonymized patient specimens requires the implementation of a mechanism to permit patients to elect not to have their specimen used. When identifiers are not removed, informed consent for the reuse of the specimen must be obtained (Schwartz et al., 1999, Clin. Chem. 45:739–745). The constructs disclosed herein relieve the laboratory of the complicated responsibility of creating a system to handle complex patient consent issues.

The synthetic control constructs disclosed herein can be produced within stably encapsulated constructs so that all phases of genetic assays, including DNA extraction processes, can be monitored. Application of techniques developed previously can be used to stabilize *E. coli* containing the constructs so that they can be processed through most routine extraction procedures used for whole blood (see, e.g., U.S. Pat. No. 6,074,825 and No. 5,994,078). Constructs can be encapsulated and bound so that they mimic buccal cells and dried blood spots. These two specimen types are particularly important in CF testing because they are noninvasive, easy to obtain, transport, and handle, and therefore likely to be the specimens of choice for high throughput screening tests for newborns and carrier status. Cell lines are another source of control material currently used for quality assurance of genetic tests. The American Type Culture Collection web site lists few cell lines carrying the CFTR gene; others are available at the Human Mutant Cell Repository (Coriell Institute, Camden, N.J.). However, not all CF mutations are represented in these cells (Riordan et. al., 1989, Science 245:1066–1073). Even if it were practical to develop a cell line for each genotype, cell lines can be difficult for clinical laboratories to handle. The cultures must be maintained using stringent tissue culture techniques so that the desired characteristics are retained and contamination with bacteria and mycoplasma is avoided (Kerem et al, 1989, Science 245:1073–1080). The constructs disclosed herein avoid these problems. That is, the methods of the invention allow construction of a single construct which can comprise any or several genotypes.

Additionally, techniques have been developed which can be used to encapsulate or bind the constructs with a binding agent such as, but not limited to, cationic lipids and liposomes, polyamines (e.g., nylon), siliceous compounds (e.g., silica gel, fumed silica, diatomaceous earth, glass particles, amine-modified silica, and the like), zeolites (e.g., low alumina zeolyte), polystyrene (e.g., amine-modified polystyrene, carboxy-polystyrene particles, and the like), glucosamines and glucosamine derivatives (e.g., chitin, chitosan, and the like), and all the combinations of the above compounds, thus producing robust and stable control reference standards. In sum, the data disclosed herein demonstrate the production of comprehensive, stable, maintenance-free, and ready-to-use control DNA constructs which obviate the need for difficult to obtain patient-derived material, sophisticated tissue culture techniques, and can be used under field conditions which prevent use of cellular/viral-derived materials.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated control DNA construct comprising a vector portion for expression in a cell and a target nucleic acid comprising two or more nucleic acid fragments wherein each fragment specifies a component associated with at least one of a disease state, an environmental condition, or a biological organism, wherein said component is different from a component specified by any other fragment present elsewhere in said construct, and wherein the 5'-most fragment is linked to said vector portion via a restriction site not present elsewhere in said construct, and wherein the 3'-most fragment is linked to said vector portion via a restriction site not present elsewhere in said construct, and further wherein each said fragment is flanked by a restriction site not present elsewhere in said construct, wherein each of said fragments comprise at least one exon of a gene, wherein said exon is a cystic fibrosis transmembrane conductance regulator (CFTR) exon, further wherein said CFTR exon is selected from the group consisting of exon 10 and exon 11, and wherein said restriction site is selected from the group consisting of a BssH II site, a Csp45 I site, a Age I site, and a Nco I site.

2. The isolated control DNA construct of claim 1, wherein said restriction site linking said 5'-most fragment to said vector portion is BssH II.

3. The isolated control DNA construct of claim 2, wherein said 5'-most fragment is CFTR exon 10.

4. The isolated control DNA construct of claim 1, wherein said restriction site linking said 3'-most fragment to said vector portion is Age I.

5. The isolated control DNA construct of claim 4, wherein said 3'-most fragment is CFTR exon 11.

6. The isolated control DNA construct of claim 5, wherein said restriction site linking said 3' and 5' ends of each of said fragments within said construct is Csp45 I.

7. The isolated control DNA construct of claim 3, wherein said exon 10 comprises a mutation or polymorphism associated with cystic fibrosis.

8. The isolated control DNA construct of claim 7, wherein said mutation is selected from the group consisting of a G480C mutation, a DI507 mutation, and a DF508 mutation.

9. The isolated control DNA construct of claim 7, wherein said polymorphism is selected from the group consisting of a F508C polymorphism, a I507V polymorphism, and a I506V polymorphism.

10. The isolated control DNA construct of claim 5, wherein said exon 11 comprises a mutation or polymorphism associated with cystic fibrosis.

11. The isolated control DNA construct of claim 10, wherein said mutation is selected from the group consisting of a G542X mutation, a G551D mutation, an R553X mutation, an A559T mutation, and an R560T mutation.

12. The isolated control DNA construct of claim 10, wherein said polymorphism is selected from the group consisting of a F508C polymorphism, a I507V polymorphism, and a I506V polymorphism.

13. An isolated control DNA construct comprising a vector portion for expression in a cell and a target nucleic acid comprising two or more nucleic acid fragments wherein each fragment specifies a component associated with at least one of a disease state, an environmental condition, or a biological organism, wherein said component is different from a component specified by any other fragment present elsewhere in said construct, and wherein the 5'-most fragment is linked to said vector portion via a restriction site not present elsewhere in said construct, and wherein the 3'-most fragment is linked to said vector portion via a restriction site not present elsewhere in said construct, and further wherein each said fragment is flanked by a restriction site not present elsewhere in said construct, wherein said fragments comprise a nucleic acid selected from the group consisting of a *Giardia lamblia* nucleic acid, a *Cryptosporidium parvum* nucleic acid, a human immunodeficiency virus nucleic acid, a hepatitis C virus nucleic acid, a factor V nucleic acid, a *Chlamydia trachomatis* nucleic acid, a *Mycobacterium tuberculosis* nucleic acid, a nucleic acid associated with hereditary hemochromatosis, a parvovirus B19 nucleic acid, a lipoprotein lipase gene, a methyltetrahydrofolate reductase gene, a beta cystathionase synthetase nucleic acid, a Factor II nucleic acid, a Factor VII nucleic acid, a Factor VIII nucleic acid, Factor IX nucleic acid, a prothrombin nucleic acid, and a nucleic acid comprising a translocation associated with hematologic disease, wherein said nucleic acid comprising a translocation associated with hematologic disease is a BCR/abl nucleic acid.

* * * * *

SEQUENCE LISTING

```
<160> NUMBER OF SEQ ID NOS: 10

<210> SEQ ID NO 1
<211> LENGTH: 18
<212> TYPE: DNA
<213> ORGANISM: Homo sapiens

<400> SEQUENCE: 1
aacagcgcgc gacacaga                                              18

<210> SEQ ID NO 2
<211> LENGTH: 27
<212> TYPE: DNA
<213> ORGANISM: Homo sapiens

<400> SEQUENCE: 2
ccatttcgaa aaatgcattt attgtga                                    27

<210> SEQ ID NO 3
<211> LENGTH: 23
<212> TYPE: DNA
<213> ORGANISM: Homo sapiens

<400> SEQUENCE: 3
gcattcgaaa taatggagat gca                                        23

<210> SEQ ID NO 4
<211> LENGTH: 22
<212> TYPE: DNA
<213> ORGANISM: Homo sapiens

<400> SEQUENCE: 4
caaaccggta cactgacacc aa                                         22

<210> SEQ ID NO 5
<211> LENGTH: 38
<212> TYPE: DNA
<213> ORGANISM: Homo sapiens

<400> SEQUENCE: 5
gcctggcacc attaaagaaa atatctttgg tgtctatg                        38

<210> SEQ ID NO 6
<211> LENGTH: 41
<212> TYPE: DNA
<213> ORGANISM: Homo sapiens
```

-continued

```
<400> SEQUENCE: 6
cataggaaac accaaagata ttttctttaa tggtgccagg c                    41

<210> SEQ ID NO 7
<211> LENGTH: 44
<212> TYPE: DNA
<213> ORGANISM: Homo sapiens

<400> SEQUENCE: 7
gcctggcacc attaaagaaa atatcatcgg tgtttcctat gatg                 44

<210> SEQ ID NO 8
<211> LENGTH: 44
<212> TYPE: DNA
<213> ORGANISM: Homo sapiens

<400> SEQUENCE: 8
catcatagga aacaccgatg atattttctt taatggtgcc aggc                 44

<210> SEQ ID NO 9
<211> LENGTH: 795
<212> TYPE: DNA
<213> ORGANISM: Homo sapiens

<400> SEQUENCE: 9
aacagcgcgc gacacagagt gagcacttgg caactgttag ctgttactaa ccttccccat    60
tcttcctcca aacctattcc aactatctga atcatgtgcc ccttctctgt gaacctctat   120
cataatactt gtcacactgt attgtaattg tctcttttac tttcccttgt atcttttgtg   180
catagcagag tacctgaaac aggaagtatt ttaaatattt tgaatcaaat gagttaatag   240
aatctttaca aataagaata tacacttctg cttaggatga taattggagg caagtgaatc   300
ctgagcgtga tttgataatg acctaataat gatgggtttt atttccagac ttcacttcta   360
atggtgatta tgggagaact ggagccttca gagggtaaaa ttaagcacag tggaagaatt   420
tcattctgtt ctcagttttc ctggattatg cctggcacca ttaaagaaaa tatcatcttt   480
ggtgtttcct atgatgaata tagatacaga agcgtcatca aagcatgcca actagaagag   540
gtaagaaact atgtgaaaac ttttgatta tgcatatgaa cccttcacac tacccaaatt    600
atatatttgg ctccatattc aatcggttag tctacatata tttatgtttc ctctatgggt   660
aagctactgt gaatggatca attaataaaa cacatgacct atgctttaag aagcttgcaa   720
acacatgaaa taaatgcaat ttattttta aataatgggt tcatttgatc acaataaatg    780 cattttcga aatgg                                                    795

<210> SEQ ID NO 10
<211> LENGTH: 490
<212> TYPE: DNA
<213> ORGANISM: Homo sapiens

<400> SEQUENCE: 10
gcattcgaaa taatggagat gcaatgttca aaatttcaac tgtggttaaa gcaatagtgt    60
gatatatgat tacattagaa ggaagatgtg cctttcaaat tcagattgag catactaaaa   120
gtgactctct aattttctat ttttggtaat aggacatctc caagtttgca gagaaagaca   180
atatagttct tggagaaggt ggaatcacac tgagtggagg tcaacgagca agaatttctt   240
tagcaaggtg aataactaat tattggtcta gcaagcattt gctgtaaatg tcattcatgt   300
aaaaaaatta cagacatttc tctattgctt tatattctgt ttctggaatt gaaaaaatcc   360
```

-continued

```
tggggttttta tggctagtgg gttaagaatc acatttaaga actataaata atggtatagt    420
atccagattt ggtagagatt atggttactc agaatctgtg cccgtatctt ggtgtcagtg    480
taccggtttg                                                           490
```